United States Patent
Mandelboim et al.

(10) Patent No.: US 10,716,864 B2
(45) Date of Patent: Jul. 21, 2020

(54) ANTI-NKP46 ANTIBODIES, TOXIN CONJUGATES, AND THERAPEUTIC USE OF SAME

(71) Applicants: Yissum Research Development Company of the Hebrew University of Jerusalem Ltd., Jerusalem (IL); University of Rijeka Faculty of Medicine, Rijeka (HR)

(72) Inventors: Ofer Mandelboim, Shoham (IL); Stipan Jonjic, Viskovo (HR); Orit Berhani, Jerusalem (IL); Ariella Glasner, Jerusalem (IL)

(73) Assignees: YISSUM RESEARCH DEVELOPMENT COMPANY OF THE HEBREW UNIVERSITY OF JERUSALEM LTD., Jerusalem (IL); UNIVERSITY OF RIJEKA FACULTY OF MEDICINE, Rijeka (HR)

( * ) Notice: Subject to any disclaimer, the term of this patent is extended or adjusted under 35 U.S.C. 154(b) by 254 days.

(21) Appl. No.: 15/920,765

(22) Filed: Mar. 14, 2018

(65) Prior Publication Data
US 2018/0207290 A1 Jul. 26, 2018

Related U.S. Application Data

(63) Continuation-in-part of application No. PCT/IL2017/050842, filed on Jul. 28, 2017.

(60) Provisional application No. 62/384,267, filed on Sep. 7, 2016.

(51) Int. Cl.
| | | |
|---|---|---|
| A61K 39/00 | (2006.01) |
| C07K 16/00 | (2006.01) |
| C07K 16/28 | (2006.01) |
| A61K 39/395 | (2006.01) |
| A61K 51/10 | (2006.01) |
| G01N 33/574 | (2006.01) |
| A61P 35/00 | (2006.01) |
| A61K 47/68 | (2017.01) |
| A61P 3/08 | (2006.01) |

(52) U.S. Cl.
CPC ........... *A61K 47/6803* (2017.08); *A61P 3/08* (2018.01); *A61P 35/00* (2018.01); *C07K 16/2803* (2013.01); *G01N 33/57484* (2013.01); *A61K 2039/505* (2013.01); *C07K 2317/77* (2013.01); *G01N 2800/042* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,940,475 | A | 2/1976 | Gross |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,289,747 | A | 9/1981 | Chu |
| 4,376,110 | A | 3/1983 | David et al. |
| 4,666,828 | A | 5/1987 | Gusella |
| 4,683,202 | A | 7/1987 | Mullis |
| 4,801,531 | A | 1/1989 | Frossard |
| 4,816,567 | A | 3/1989 | Cabilly et al. |
| 4,873,316 | A | 10/1989 | Meade et al. |
| 4,879,219 | A | 11/1989 | Wands et al. |
| 5,011,771 | A | 4/1991 | Bellet et al. |
| 5,192,659 | A | 3/1993 | Simons |
| 5,272,057 | A | 12/1993 | Smulson et al. |
| 5,281,521 | A | 1/1994 | Trojanowski et al. |
| 5,545,806 | A | 8/1996 | Lonberg et al. |

(Continued)

FOREIGN PATENT DOCUMENTS

| | | |
|---|---|---|
| EP | 0264166 A1 | 4/1988 |
| EP | 2861741 B1 | 4/2017 |

(Continued)

OTHER PUBLICATIONS

Marks et al., "By-passing immunization. Human antibodies from V-gene libraries displayed on phage", J Mol Biol, (1991), 222(3): 581-597.

(Continued)

*Primary Examiner* — Julie Wu
(74) *Attorney, Agent, or Firm* — Rothwell, Figg, Ernst & Manbeck, P.C.

(57) ABSTRACT

An affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16 is disclosed. A pharmaceutical compositions comprising as an active ingredient the affinity binding moiety is also disclosed. Methods of diagnosing, preventing or treating an autoimmune disease or a cancer associated with an expression of NKp46 are also disclosed.

37 Claims, 7 Drawing Sheets
(5 of 7 Drawing Sheet(s) Filed in Color)
Specification includes a Sequence Listing.

(56) References Cited

U.S. PATENT DOCUMENTS

| | | | |
|---|---|---|---|
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,959,177 | A | 9/1999 | Hein et al. |
| 6,040,498 | A | 3/2000 | Stomp et al. |
| 6,417,429 | B1 | 7/2002 | Hein et al. |
| 6,420,548 | B1 | 7/2002 | Vezina et al. |
| 7,125,978 | B1 | 10/2006 | Vézina et al. |
| 9,078,931 | B2 | 7/2015 | Satpayev et al. |
| 2008/0145895 | A1 | 6/2008 | Horwitz |
| 2012/0178126 | A1 | 7/2012 | Horwitz |

FOREIGN PATENT DOCUMENTS

| | | |
|---|---|---|
| WO | WO 2005/000086 | 1/2005 |
| WO | WO 2014/125041 | 8/2014 |
| WO | WO 2015/015489 | 2/2015 |
| WO | WO 2015/197593 | 12/2015 |
| WO | 2017027325 A1 | 2/2017 |
| WO | WO 2018/047154 | 3/2018 |

OTHER PUBLICATIONS

Marks et al., "By-passing immunization: building high affinity human antibodies by chain shuffling", Biotechnology (NY), (1992), 10(7): 779-783.

Mather, "Establishment and characterization of two distinct mouse testicular epithelial cell lines", Biol Reprod, (1980), 23(1): 243-252.

Mather et al., "Culture of testicular cells in hormone-supplemented serum-free medium", Ann NY Acad Sci, (1982), 383: 44-68.

Matsuura et al., "Antiphospholipid antibodies and atherosclerosis", Lupus 7 Suppl, (1998), 2: S135-S139.

Mitsuma, "Idiopathic myxedema and blocking type antibodies to TSH receptor", Nihon Rinsho, (1999), 57(8): 1759-1763. Abstract.

Moccia, "Two cases of autoimmune thrombocytopenic purpura associated with antiphospholipid antibodies", Ann Ital Med Int, (1999), 14(2): 114-117. Abstract.

Moore et al., "Noninvasive in vivo measurement of beta-cell mass in mouse model of diabetes", Diabetes, (2001), 50 (10): 2231-2236.

Morrison, "Immunology. Success in specification", Nature, (1994), 368(6474): 812-813.

Neuberger, "Generating high-avidity human Mabs in mice", Nat Biotechnol, (1996), 14(7): 826.

Nobile-Orazio et al., "Diagnostic relevance of anti-neural antibodies in dysimmune neuropathies", Electroencephalogr Clin Neurophysiol Suppl, (1999), 50: 419-427.

Noel, "Antineutrophil cytoplasm antibodies (ANCA): description and immunopathological role", Ann Med Interne (Paris), (2000), 151(3): 178-183. Abstract.

Orgiazzi, "Anti-TSH receptor antibodies in clinical practice", Endocrinol Metab Clin North Am, (2000), 29(2): 339-355.

Oron et al., "Animal model and in vitro studies of anti neurofilament antibodies mediated neurodegeneration in Alzheimer's disease", J Neural Transm Suppl, (1997), 49: 77-84.

Oshima et al., "Autoimmune T cell recognition of human acetylcholine receptor: the sites of T cell recognition in myasthenia gravis on the extracellular part of the alpha subunit", Eur J Immunol, (1990), 20(12): 2563-2569.

Pinkert et al., "An albumin enhancer located 10 kb upstream functions along with its promoter to direct efficient, liver-specific expression in transgenic mice", Genes Dev, (1987), 1(3): 268-276.

Praprotnik et al., "Pathogenic role of anti-endothelial cell antibodies in systemic vasculitis", Wien Klin Wochenschr, (2000), 112(15-16): 660-664.

Presta, "Antibody engineering", Curr Op Struct Biol, (1992), 2(4): 593-596.

Reiner et al., "Accurate measurement of pancreatic islet beta-cell mass using a second-generation fluorescent exendin-4 analog", Proc Natl Acad Sci USA, (2011), 108(31): 12815-12820.

Renaudineau et al., "Anti-endothelial cell antibodies in systemic sclerosis", Clin Diagn Lab Immunol, (1999), 6(2): 156-160.

Riechmann et al., "Reshaping human antibodies for therapy", Nature, (1988), 332(6162): 323-327.

Sakata et al., "Autoimmune T-cell recognition sites of human thyrotropin receptor in Graves' disease", Mol Cell Endocrinol, (1993), 92(1): 77-82.

Sallah et al., "Gamma/delta T-cell hepatosplenic lymphoma: review of the literature, diagnosis by flow cytometry and concomitant autoimmune hemolytic anemia", Ann Hematol, (1997), 74(3): 139-142.

Scarano et al., "Surface plasmon resonance imaging for affinity-based biosensors", Biosens Bioelectron, (2010), 25(5): 957-966.

Semple et al., "Differences in serum cytokine levels in acute and chronic autoimmune thrombocytopenic purpura: relationship to platelet phenotype and antiplatelet T-cell reactivity", Blood, (1996), 87(10): 4245-4254.

Söderström et al., "Autoimmune T cell repertoire in optic neuritis and multiple sclerosis: T cells recognising multiple myelin proteins are accumulated in cerebrospinal fluid", J Neurol Neurosurg Psychiatry, (1994), 57(5): 544-551.

Strassburg et al., "Anti-mitochondrial antibodies and other immunological tests in primary biliary cirrhosis", Eur J Gastroenterol Hepatol, (1999), 11(6): 595-601.

Suresh et al., "Bispecific monoclonal antibodies from hybrid hybridomas", Methods Enzymol, (1986), 121: 210-228.

Takamori et al., "Antibodies to calcium channel and synaptotagmin in Lambert-Eaton myasthenic syndrome", Am J Med Sci, (2000), 319(4): 204-208.

Tincani et al., "Anti beta2-glycoprotein I antibodies: clinical significance", Lupus 7 Suppl, (1998), 2: S107-S109.

Tisch and McDevitt, "Antigen-specific immunotherapy: is it a real possibility to combat T-cell-mediated autoimmunity?", Proc Natl Acad Sci USA, (1994), 91(2): 437-438.

Toyoda et al., "Anti-thyroglobulin antibodies", Nihon Rinsho, (1999), 57(8): 1810-1814. Abstract.

Urlaub and Chasin, "Isolation of Chinese hamster cell mutants deficient in dihydrofolate reductase activity", Proc Natl Acad Sci USA, (1980), 77(7): 4216-4220.

Vaarala, "Antiphospholipid antibodies and myocardial infarction", Lupus, (1998), 7 Suppl 2: S132-S134.

Verhoeyen et al., "Reshaping human antibodies: grafting an antilysozyme activity", Science, (1988), 239(4847): 1534-1536.

Vincent et al., "Antibodies affecting ion channel function in acquired neuromyotonia, in seropositive and seronegative myasthenia gravis, and in antibody-mediated arthrogryposis multiplex congenita", Ann NY Acad Sci, (1998), 841: 482-496.

Voswinkel et al., "B lymphocyte involvement in ankylosing spondylitis: the heavy chain variable segment gene repertoire of B lymphocytes from germinal center-like foci in the synovial membrane indicates antigen selection", Arthritis Res, (2001), 3(3):189-195.

Wallukat et al., "Agonist-like beta-adrenoceptor antibodies in heart failure", Am J Cardiol, (1999), 83(12A): 75H-79H.

Winoto and Baltimore, "A novel, inducible and T cell-specific enhancer located at the 3' end of the T cell receptor alpha locus", EMBO J, (1989). 8(3):729-733.

Yamin et al., "HCMV vCXCL1 Binds Several Chemokine Receptors and Preferentially Attracts Neutrophils over NK cells by Interacting with CXCR2", Cell Rep, (2016), 15(7): 1542-1553.

Yoo et al., "Epitope specificity and T cell receptor usage in type II collagen induced autoimmune ear disease", Cell Immunol, (1994), 157(1):249-262.

Zauli et al., "Auto-antibodies in hepatitis C", Biomed Pharmacother, (1999), 53(5-6): 234-241.

Zimmet, "Antibodies to glutamic acid decarboxylase in the prediction of insulin dependency", Diabetes Res Clin Pract, (1996), 34 Suppl: S125-S131.

Achdout et al., "Enhanced recognition of human NK receptors after influenza virus infection", J. Immunol, (2003), 171 (2): 915-923.

Alexander et al., "Autoimmune prostatitis: evidence of T cell reactivity with normal prostatic proteins", Urology, (1997), 50(6): 893-899.

(56) References Cited

OTHER PUBLICATIONS

Alter et al., "CD107a as a functional marker for the identification of natural killer cell activity", J. Immunol Methods, (2004), 294(1-2): 15-22.
Antignani and Fitzgerald, "Immunotoxins: the role of the toxin", Toxins (Basel), (2013) 5(8): 1486-1502.
Antoine and Honnorat, Anti-neuronal antibodies and central nervous system diseases: contribution to diagnosis and pathophysiology, Rev Neurol (Paris), (2000),156(1): 23-33. Abstract.
Banerji et al., "A lymphocyte-specific cellular enhancer is located downstream of the joining region in immunoglobulin heavy chain genes", Cell, (1983), 33(3): 729-740.
Berhani et al., "Human anti-NKp46 antibody for studies of NKp46-dependent NK cell function and its applications for type 1 diabetes and cancer research", Eur J Immunol (2018) doi:10.1002/eji.201847611; 14 pages.
Boerner et al., "Production of antigen-specific human monoclonal antibodies from in vitro-primed human splenocytes", J Immunol, (1991), 147(1): 86-95.
Braley-Mullen and Yu, Early requirement for B cells for development of spontaneous autoimmune thyroiditis in NOD. H-2h4 mice, J Immunol, (2000), 165(12): 7262-7269.
Byrne and Ruddle, "Multiplex gene regulation: a two-tiered approach to transgene regulation in transgenic mice" Proc Natl Acad Sci USA, (1989), 86(14): 5473-5477.
Calame and Eaton, "Transcriptional controlling elements in the immunoglobulin and T cell receptor loci", Adv Immunol, (1988), 43: 235-275.
Caporossi et al., "Autoimmune T-cell response to the CD4 molecule in HIV-infected patients",Viral Immunol, (1998), 11 (1): 9-17.
Castaño and Eisenbarth, "Type-I diabetes: a chronic autoimmune disease of human, mouse, and rat", Annu Rev Immunol, (1990), 8: 647-679.
Chan et al., "The central and multiple roles of B cells in lupus pathogenesis", Immunol Rev, (1999), 169: 107-121.
Chaushu et al., "Direct recognition of Fusobacterium nucleatum by the NK cell natural cytotoxicity receptor NKp46 aggravates periodontal disease", PLoS Pathog, (2012), 8(3): e1002601; 12 pages.
Christmas, "Gamma delta T lymphocyte clonality in pure red blood cell aplasia", Blood, (1991), 77(5): 1127.
Cross et al., "B cells and antibodies in CNS demyelinating disease", J Neuroimmunol, (2001), 112(1-2): 1-14.
Cunha-Neto et al., "Autoimmunity in Chagas' disease. Identification of cardiac myosin-B13 Trypanosoma cruzi protein crossreactive T cell clones in heart lesions of a chronic Chagas' cardiomyopathy patient", J Clin Invest, (1996), 98(8): 1709-1712.
Diekman et al., "Anti-sperm antibodies from infertile patients and their cognate sperm antigens: a review. Identity between SAGA-1, the H6-3C4 antigen, and CD52", Am J Reprod Immunol, (2000), 43(3): 134-143.
Edlund et al., "Cell-specific expression of the rat insulin gene: evidence for role of two distinct 5' flanking elements", Science, (1985), 230(4728): 912-916.
Efremov et al., "The pathologic significance of the immunoglobulins expressed by chronic lymphocytic leukemia B-cells in the development of autoimmune hemolytic anemia", Leuk Lymphoma, (1998), 28(3-4): 285-293.
Erikson et al., "Self-reactive B cells in nonautoimmune and autoimmune mice", Immunol Res, (1998), 17(1-2): 49-61.
Feist et al., "Diagnostic importance of anti-proteasome antibodies", Int Arch Allergy Immunol, (2000), 123(1): 92-97.
Fishwild et al., "High-avidity human IgG kappa monoclonal antibodies from a novel strain of minilocus transgenic mice", Nat Biotechnol, (1996), 14(7): 845-851.
Flamholz et al., "Therapeutic plasma exchange for the acute management of the catastrophic antiphospholipid syndrome: beta(2)-glycoprotein I antibodies as a marker of response to therapy", J Clin Apher, (1999), 14(4): 171-176.
Franco et al., "Liver-derived T cell clones in autoimmune chronic active hepatitis: accessory cell function of hepatocytes expressing class II major histocompatibility complex molecules", Clin Immunol Immunopathol, (1990), 54(3): 382-394.
Garcia Herola et al., "Antineutrophil cytoplasmic antibodies (ANCA) in chronic inflammatory intestinal disease", Gastroenterol Hepatol, (2000), 23(1): 16-23. With machine translation.
Garza et al., "Mechanism of ovarian autoimmunity: induction of T cell and antibody responses by T cell epitope mimicry and epitope spreading", J Reprod Immunol, (1998), 37(2): 87-101.
Gerngross, "Advances in the production of human therapeutic proteins in yeasts and filamentous fungi", Nat Biotechnol, (2004), 22(11): 1409-1414.
Gloddek et al., "Induction of an inner-ear-specific autoreactive T-cell line for the diagnostic evaluation of an autoimmune disease of the inner ear", Ann N Y Acad Sci, (1997), 830: 266-276.
Graham et al., "Characteristics of a human cell line transformed by DNA from human adenovirus type 5", J Gen Virol, (1977), 36(1): 59-72.
Gur et al., "Recognition and killing of human and murine pancreatic beta cells by the NK receptor NKp46", J Immunol, (2011), 187(6): 3096-3103.
Hara et al., "Human gamma delta T-cell receptor-positive cell-mediated inhibition of erythropoiesis in vitro in a patient with type I autoimmune polyglandular syndrome and pure red blood cell aplasia", Blood, (1990), 75(4): 941-950.
Hiemstra et al., "Cytomegalovirus in autoimmunity: T cell crossreactivity to viral antigen and autoantigen glutamic acid decarboxylase", Proc Natl Acad Sci U S A, (2001), 98(7): 3988-3991.
Hoogenboom and Winter, "By-passing immunisation. Human antibodies from synthetic repertoires of germline VH gene segments rearranged in vitro", J Mol Biol, (1992), 227(2): 381-388.
Infante and Kraig, "Myasthenia gravis and its animal model: T cell receptor expression in an antibody mediated autoimmune disease", Int Rev Immunol, (1999), 18(1-2): 83-109.
Jones, "T-cell autoimmunity in primary biliary cirrhosis", Clin Sci (Lond), (1996), 91(5): 551-558.
Jones et al., "Replacing the complementarity-determining regions in a human antibody with those from a mouse", Nature, (1986), 321(6069): 522-525.
Kelly, "T cell regulation of autoimmune interstitial nephritis", J Am Soc Nephrol, (1990), 1(2): 140-149.
Komberg, "Anti-GM1 ganglioside antibodies: their role in the diagnosis and pathogenesis of immune-mediated motor neuropathies", J Clin Neurosci, (2000), 7(3): 191-194.
Krenn et al., "Histopathology and molecular pathology of synovial B-lymphocytes in rheumatoid arthritis", Histol Histopathol, (2000), 15(3): 791-798.
Kusunoki, "Antiglycolipid antibodies in Guillain-Barré syndrome and autoimmune neuropathies", Am J Med Sci, (2000), 319(4): 234-239.
Lacroix-Desmazes et al., "Natural antibodies to factor VIII", Semin Thromb Hemost, (2000), 26(2): 157-165.
Landau and Shoenfeld, "And nevertheless . . . autoimmunity—celiac disease and the antibodies to tissue transglutaminase", Harefuah, (2000), 138(2): 122-126. With translated title.
Li et al., "Optimization of humanized IgGs in glycoengineered Pichia pastoris", Nat Biotechnol, (2006), 24(2): 210-215.
Lonberg and Huszar, "Human antibodies from transgenic mice", Int Rev Immunol, (1995), 13(1): 65-93.
Lonberg et al., "Antigen-specific human antibodies from mice comprising four distinct genetic modifications", Nature, (1994), 368(6474): 856-859.
Mandelboim et al., "Human CD16 as a lysis receptor mediating direct natural killer cell cytotoxicity", Proc Natl Acad Sci USA, (1999), 96(10): 5640-5644.
Mandelboim et al., "Recognition of haemagglutinins on virus-infected cells by NKp46 activates lysis by human NK cells", Nature, (2001), 409(6823): 1055-1060.
Manns, "Antibodies to soluble liver antigen: specific marker of autoimmune hepatitis", J Hepatol, (2000), 33(2): 326-328.
International Search Report and the Written Opinion dated Oct. 17, 2017 From the International Searching Authority Re. Application No. PCT/IL2017/050842. (17 Pages).

(56) References Cited

OTHER PUBLICATIONS

Arnon et al. "The Mechanisms Controlling the Recognition of Tumor- and Virus-Infected Cells by NKp46", Blood, XP055413222, 103(2): 664-672, Published Online Sep. 22, 2003. Fig.5.
Schleinitz et al. "Natural Killer Cells in Human Autoimmune Diseases", Immunology, XP055053983, 131(4): 451-458, Dec. 1, 2010. Abstract, p. 457, l-h col., Para 1-2.
Yossef et al. "Targeting Natural Killer Cell Reactivity by Employing Antibody to NKp46: Implications for Type 1 Diabetes", PLOS One, XP055413219, 10(2): e0118936-1-e0118936-16, Feb. 26, 2015. Abstract, p. 9, Para 1—p. 10, Para 3, p. 2, Para 4, p. 4, Para 5—p. 5, Para 1.

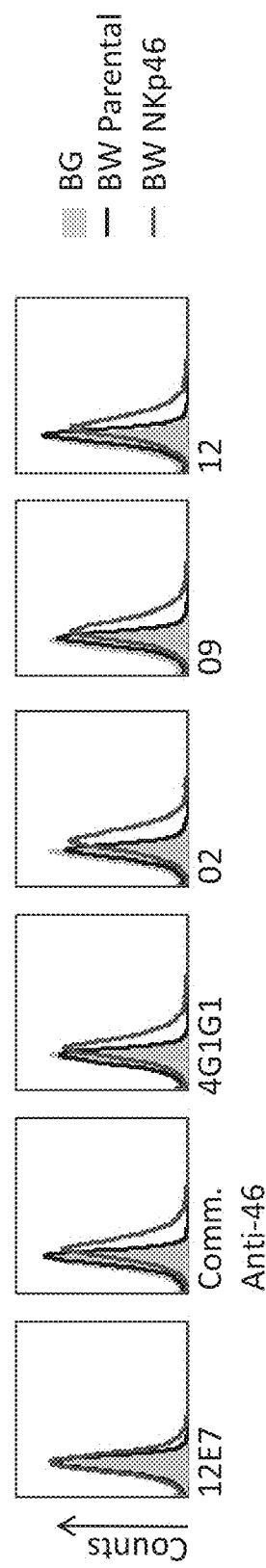
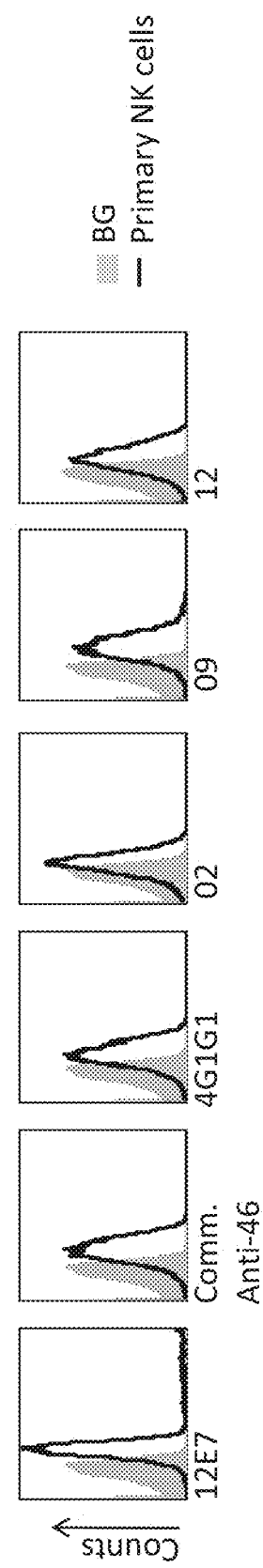
FIG. 1A
FIG. 1B

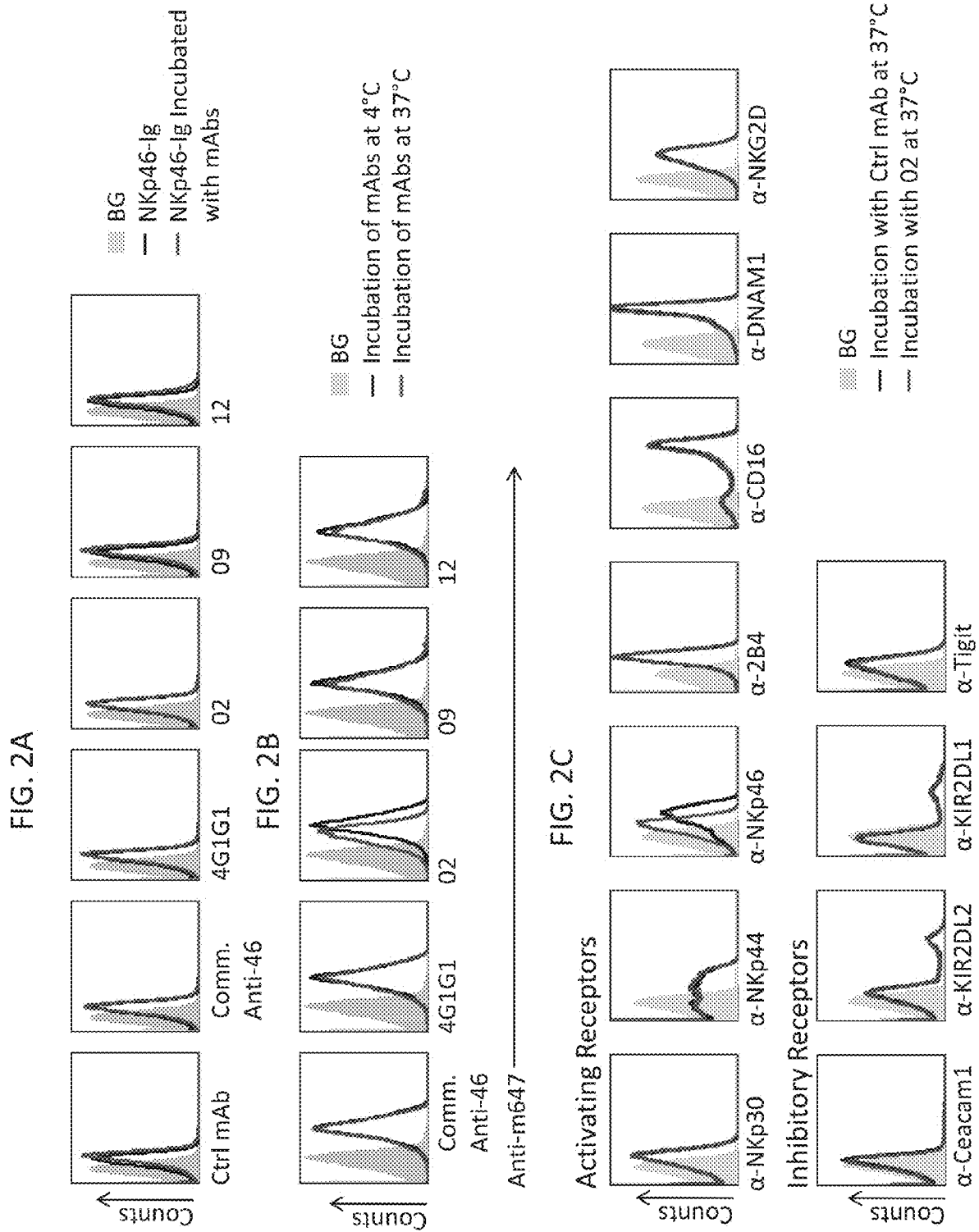

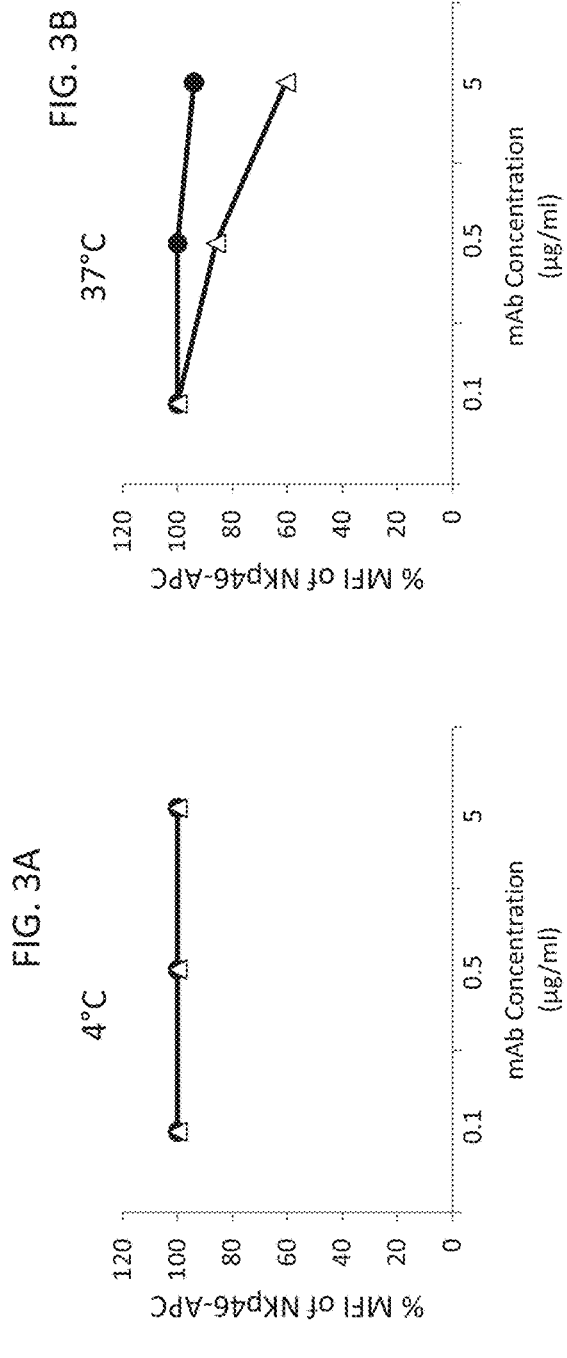
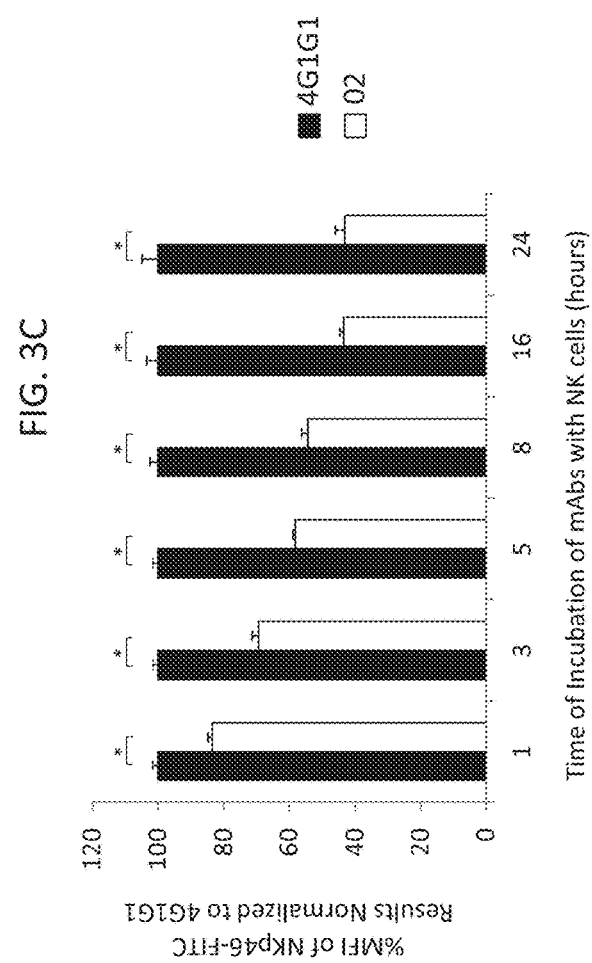
FIG. 3A
FIG. 3B
FIG. 3C

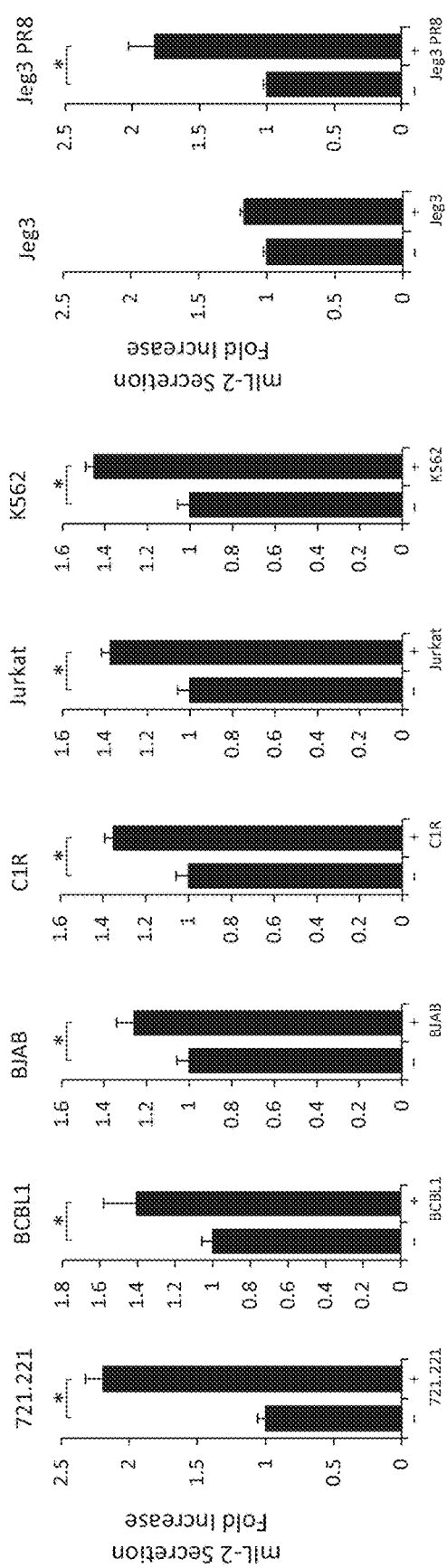
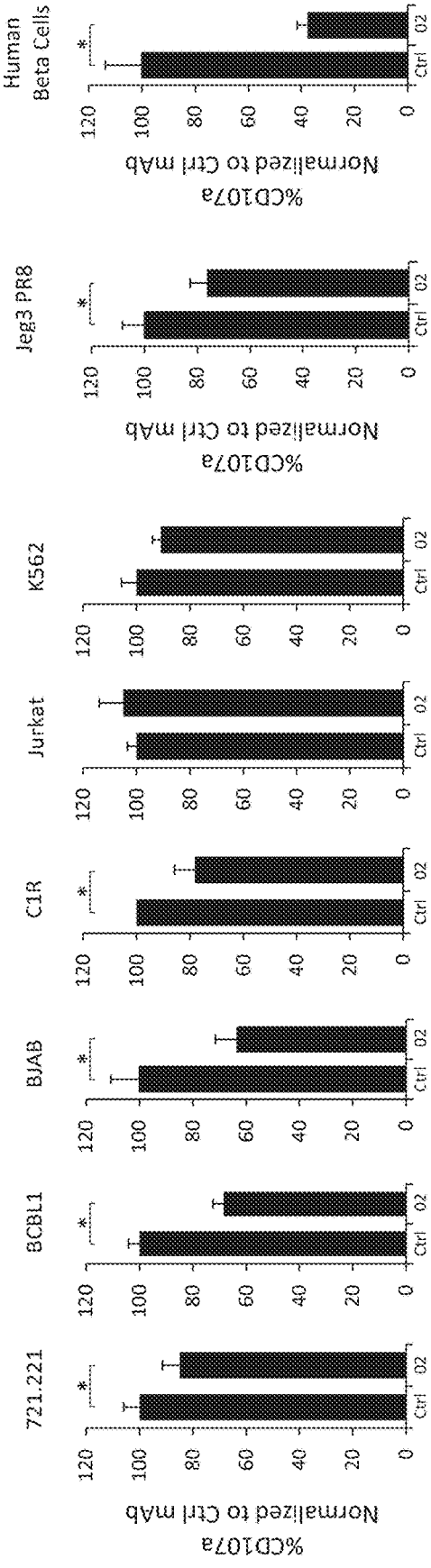
FIG. 4A, FIG. 4B, FIG. 4C, FIG. 4D, FIG. 4E

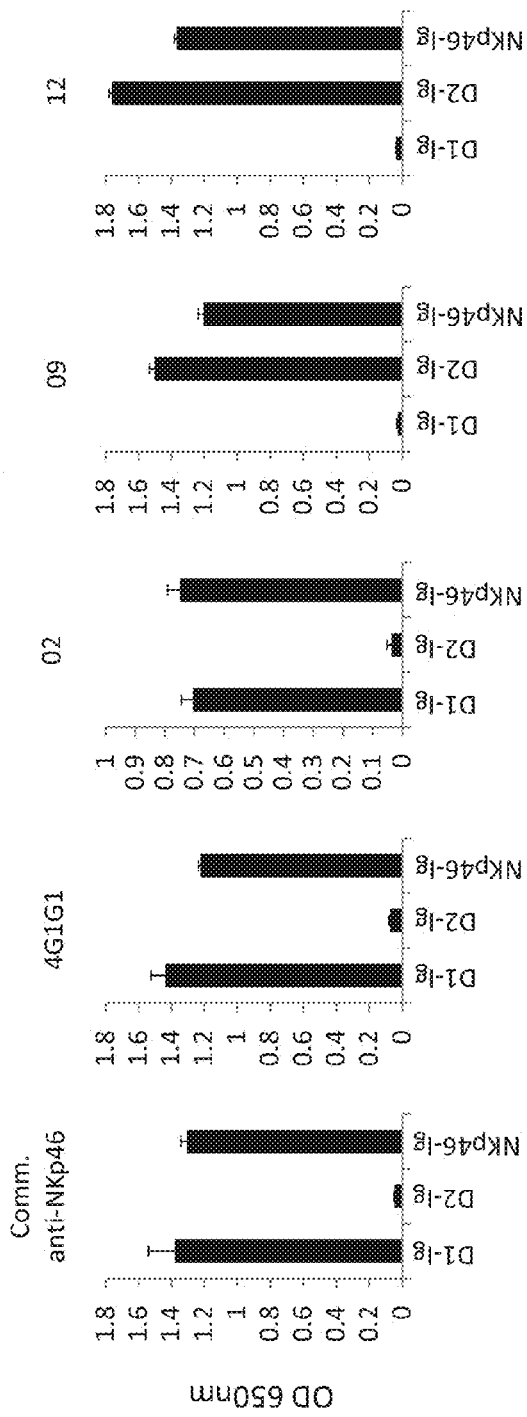
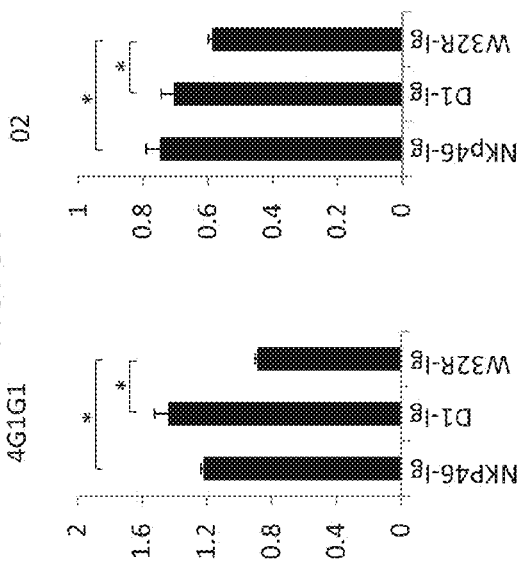
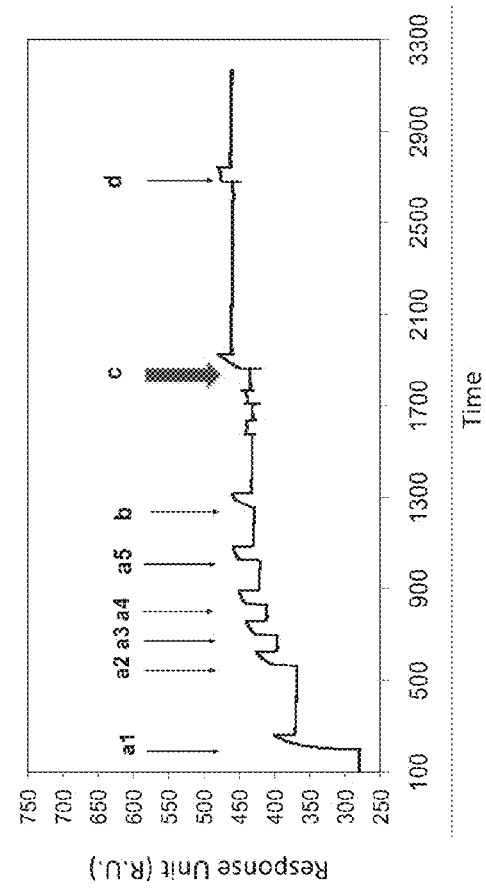

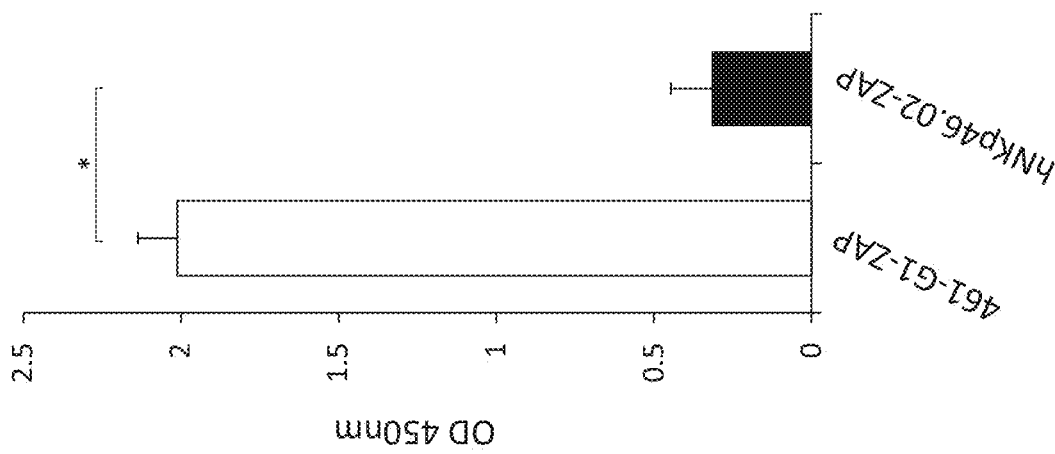
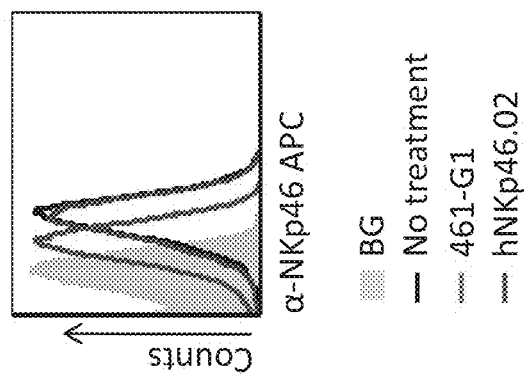
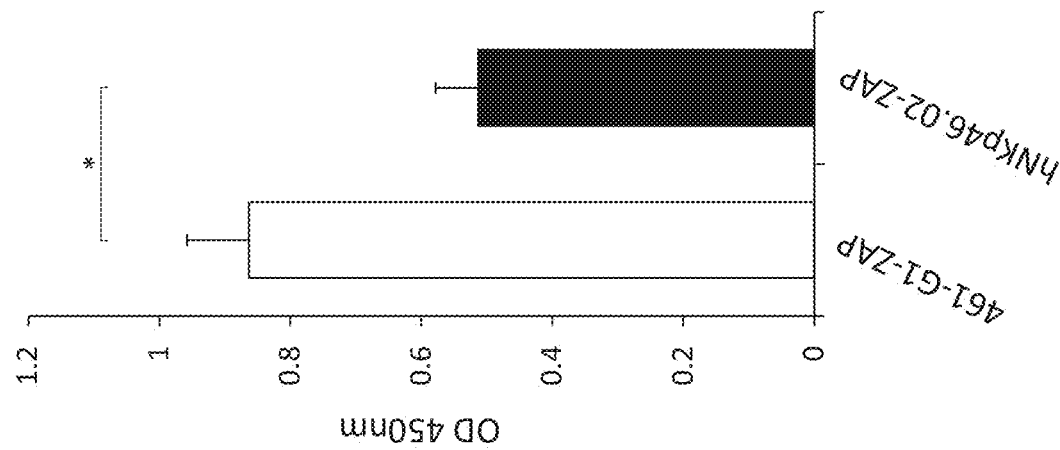
FIG. 7A
FIG. 7B
FIG. 7C

SEQUENCE LISTING

```
<160> NUMBER OF SEQ ID NOS: 16

<210> SEQ ID NO 1
<211> LENGTH: 1401
<212> TYPE: DNA
<213> ORGANISM: Artificial sequence
<220> FEATURE:
<223> OTHER INFORMATION: hNKp46.02 mAb - Heavy chain: NA sequence

<400> SEQUENCE: 1
atgggcaggc ttacttcttc attcctgcta ctgattgttc ctgcatatgt cctctcccag      60
gttactctga aagagtctgg ccctgggata ttgcagccct cccagaccct cagtctgact     120
tgttctttct ctgggttttc actgagcact tatggtatag gagtaggctg gaatcgtcag     180
ccttcaggga agggtctgga gtggctggca cacatttggt ggaatgataa tgagtactat     240
aacatagacc tgaagagccg gctcacaatc tccaaggata cctccaacaa ccaggtattc     300
ctcaagatcg ccagtgtgga cactgcagat actgccacat actactgtgt cgaggaaac      360 tataggtacg cgaggggta tgttatggac tactggggtc aaggaacctc agtcaccgtc      420
tcctcagcca aaacgacacc cccatctgtc tatccactgg ccctggatc tgctgcccaa      480 actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtccct ccagcacctg gcccagcgag      660
accgtcacct gcaacgttgc ccacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcgtctacag caagctcaat gtgcagaaga caactggga ggcaggaaat     1320 actttcacct gctctgtgtt acatgagggc ctgcacaacc accatactga aagagcctc     1380 tcccactctc ctggtaaatg a                                              1401

<210> SEQ ID NO 2
<211> LENGTH: 466
<212> TYPE: PRT
<213> ORGANISM: Artificial sequence
<220> FEATURE:
<223> OTHER INFORMATION: hNKp46.02 mAb - Heavy chain: AA sequence
```

<400> SEQUENCE: 2

```
Met Gly Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Tyr Gly Ile Gly Val Gly Trp Asn Arg Gln Pro Ser Gly Lys
        50                  55                  60

Gly Leu Glu Trp Leu Ala His Ile Trp Trp Asn Asp Asn Glu Tyr Tyr
65                  70                  75                  80

Asn Ile Asp Leu Lys Ser Arg Leu Thr Ile Ser Lys Asp Thr Ser Asn
                85                  90                  95

Asn Gln Val Phe Leu Lys Ile Ala Ser Val Asp Thr Ala Asp Thr Ala
            100                 105                 110

Thr Tyr Tyr Cys Val Arg Gly Asn Tyr Arg Tyr Ala Arg Gly Tyr Val
        115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
```

```
                    405                 410                 415
Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 3
<211> LENGTH: 21
<212> TYPE: DNA
<213> ORGANISM: Artificial sequence
<220> FEATURE:
<223> OTHER INFORMATION: hNKp46.02 mAb - Heavy chain CDR1: NA sequence

<400> SEQUENCE: 3
acttatggta taggagtagg c                                            21

<210> SEQ ID NO 4
<211> LENGTH: 7
<212> TYPE: PRT
<213> ORGANISM: Artificial sequence
<220> FEATURE:
<223> OTHER INFORMATION: hNKp46.02 mAb - Heavy chain CDR1: AA sequence

<400> SEQUENCE: 4

Thr Tyr Gly Ile Gly Val Gly
1               5

<210> SEQ ID NO 5
<211> LENGTH: 48
<212> TYPE: DNA
<213> ORGANISM: Artificial sequence
<220> FEATURE:
<223> OTHER INFORMATION: hNKp46.02 mAb - Heavy chain CDR2: NA sequence

<400> SEQUENCE: 5
cacatttggt ggaatgataa tgagtactat aacatagacc tgaagagc               48

<210> SEQ ID NO 6
<211> LENGTH: 16
<212> TYPE: PRT
<213> ORGANISM: Artificial sequence
<220> FEATURE:
<223> OTHER INFORMATION: hNKp46.02 mAb - Heavy chain CDR2: AA sequence

<400> SEQUENCE: 6

His Ile Trp Trp Asn Asp Asn Glu Tyr Tyr Asn Ile Asp Leu Lys Ser
1               5                   10                  15

<210> SEQ ID NO 7
<211> LENGTH: 39
<212> TYPE: DNA
<213> ORGANISM: Artificial sequence
<220> FEATURE:
<223> OTHER INFORMATION: hNKp46.02 mAb - Heavy chain CDR3: NA sequence

<400> SEQUENCE: 7
ggaaactata ggtacgcgag ggggtatgtt atggactac                         39

<210> SEQ ID NO 8
<211> LENGTH: 13
```

```
<212> TYPE: PRT
<213> ORGANISM: Artificial sequence
<220> FEATURE:
<223> OTHER INFORMATION: hNKp46.02 mAb - Heavy chain CDR3: AA sequence

<400> SEQUENCE: 8

Gly Asn Tyr Arg Tyr Ala Arg Gly Tyr Val Met Asp Tyr
1               5                   10

<210> SEQ ID NO 9
<211> LENGTH: 717
<212> TYPE: DNA
<213> ORGANISM: Artificial sequence
<220> FEATURE:
<223> OTHER INFORMATION: hNKp46.02 mAb - Light chain: NA sequence

<400> SEQUENCE: 9
atggagtcag acacactcct gctatgggtg ctgctgctct gggttccagg ctccactggt      60
gacattgtgc tcacccaatc tccagcttct ttggctgtgt ctctagggca gagagccacc     120
atctcctgca gagccagtga aagtgttgaa tattatggca agtttaat gcagtggtac       180 caacaaaaac caggacagcc acccaaactc ctcatctatg ctgcatccaa cgtagaatct     240
ggggtccctg ccaggtttag tggcagtggg tctgggacag acttcagcct caacatccat     300
cctgtggagg aggatgattt tgcaatgtat ttctgtcagc aaaataggaa ggttccttgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660 actcacaaga catcaacttc acccattgtc aagagcttca caggaatga gtgttag        717

<210> SEQ ID NO 10
<211> LENGTH: 238
<212> TYPE: PRT
<213> ORGANISM: Artificial sequence
<220> FEATURE:
<223> OTHER INFORMATION: hNKp46.02 mAb - Light chain: AA sequence

<400> SEQUENCE: 10

Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
            35                  40                  45

Val Glu Tyr Tyr Gly Thr Ser Leu Met Gln Trp Tyr Gln Gln Lys Pro
        50                  55                  60

Gly Gln Pro Pro Lys Leu Leu Ile Tyr Ala Ala Ser Asn Val Glu Ser
65                  70                  75                  80

Gly Val Pro Ala Arg Phe Ser Gly Ser Gly Ser Gly Thr Asp Phe Ser
                85                  90                  95

Leu Asn Ile His Pro Val Glu Glu Asp Asp Phe Ala Met Tyr Phe Cys
            100                 105                 110

Gln Gln Asn Arg Lys Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
```

```
                 130                 135                 140
Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 11
<211> LENGTH: 45
<212> TYPE: DNA
<213> ORGANISM: Artificial sequence
<220> FEATURE:
<223> OTHER INFORMATION: hNKp46.02 mAb - Light chain CDR1: NA sequence

<400> SEQUENCE: 11
agagccagtg aaagtgttga atattatggc acaagtttaa tgcag           45

<210> SEQ ID NO 12
<211> LENGTH: 15
<212> TYPE: PRT
<213> ORGANISM: Artificial sequence
<220> FEATURE:
<223> OTHER INFORMATION: hNKp46.02 mAb - Light chain CDR1: AA sequence

<400> SEQUENCE: 12

Arg Ala Ser Glu Ser Val Glu Tyr Tyr Gly Thr Ser Leu Met Gln
1               5                   10                  15

<210> SEQ ID NO 13
<211> LENGTH: 21
<212> TYPE: DNA
<213> ORGANISM: Artificial sequence
<220> FEATURE:
<223> OTHER INFORMATION: hNKp46.02 mAb - Light chain CDR2: NA sequence

<400> SEQUENCE: 13
gctgcatcca acgtagaatc t                                     21

<210> SEQ ID NO 14
<211> LENGTH: 7
<212> TYPE: PRT
<213> ORGANISM: Artificial sequence
<220> FEATURE:
<223> OTHER INFORMATION: hNKp46.02 mAb - Light chain CDR2: AA sequence

<400> SEQUENCE: 14

Ala Ala Ser Asn Val Glu Ser
1               5

<210> SEQ ID NO 15
<211> LENGTH: 27
<212> TYPE: DNA
<213> ORGANISM: Artificial sequence
<220> FEATURE:
<223> OTHER INFORMATION: hNKp46.02 mAb - Light chain CDR3: NA sequence

<400> SEQUENCE: 15
```

```
cagcaaaata ggaaggttcc ttggacg                                           27
```

```
<210> SEQ ID NO 16
<211> LENGTH: 9
<212> TYPE: PRT
<213> ORGANISM: Artificial sequence
<220> FEATURE:
<223> OTHER INFORMATION: hNKp46.02 mAb - Light chain CDR3: AA sequence

<400> SEQUENCE: 16

Gln Gln Asn Arg Lys Val Pro Trp Thr
1               5
```

ANTI-NKP46 ANTIBODIES, TOXIN CONJUGATES, AND THERAPEUTIC USE OF SAME

RELATED APPLICATIONS

This application is a Continuation-in-Part (CIP) of PCT Patent Application No. PCT/IL2017/050842 filed on Jul. 28, 2017, which claims the benefit of priority under 35 USC 119(e) of U.S. Provisional Patent Application No. 62/384, 267 filed on Sep. 7, 2016. The contents of the above applications are all incorporated by reference as if fully set forth herein in their entirety.

SEQUENCE LISTING STATEMENT

The present application includes a Sequence Listing filed in electronic format. The Sequence Listing is entitled "3596-227 ST25.txt" created on Mar. 19, 2020, and is 13,000 bytes in size. The information in the electronic format of the Sequence Listing is part of the present application and is incorporated herein by reference in its entirety.

FIELD AND BACKGROUND OF THE INVENTION

The present invention, in some embodiments thereof, relates to novel NKp46 antibodies and, more particularly, but not exclusively, to the use of same for preventing and/or treating malignant and autoimmune diseases.

Natural killer (NK) cells are innate effector lymphocytes, first identified in 1975 for their ability kill tumor cells without prior stimulation. To date, NK cells have emerged as one of the most crucial first responders to tumor transformation and viral, bacterial, or fungal infections. They are also involved in autoimmune diseases such as type I and type II diabetes. NK cells have cytotoxic activity and can secrete cytokines; hence they are part of the newly characterized family of Innate Lymphoid Cells (ILCs). They are classified as Group 1 ILCs, mainly due to their production of type 1 cytokines (IFNγ and TNFα). NK cells have the distinct ability to recognize many diverse targets due to their numerous germ-line encoded activating and inhibitory receptors. A balance of signals received by these receptors ultimately determines whether the NK cells act against a given target cell, or remain neutral.

Three activating receptors found on NK cells, NKp30, NKp44, and NKp46, are collectively known as Natural Cytotoxicity Receptors (NCRs). These receptors are crucial in NK cells antitumor and antiviral defenses. NKp46 has been established as a critical activating receptor since it is expressed almost exclusively by NK cells and is the only NCR with a mouse orthologue. Its ligand repertoire ranges from viral ligands, such as, hemagglutinin (HA) and hemagglutinin-neruamindase (HN) of influenza virus, Sendai virus, Newcastle disease virus, and poxvirus, to unknown ligands found on bacteria, such as *Fusobacterium nucleatum*, tumors, adipose cells, and human pancreatic beta cells. The identification of the unknown ligands, in particularly the tumor ligands of NKp46, has been intensely investigated for over a decade.

NKp46 is part of the IgG superfamily, and consists of two C2-type Ig-like domains: D1 is the membrane distal domain and D2 is the membrane proximal domain. Interestingly, the D1 domain was shown to not be involved in NKp46 ligand recognition, and binding was solely mediated by its D2 domain (which also contains the stalk and hinge regions). Different features within the D2 domain determine binding to various ligands. For example, there are three glycosylation sites, Asn216, Thr125 and Thr225 which are commonly involved in the binding to different ligands. HA recognition by NKp46 was shown to be sialic acid dependent, primarily mediated by the residue Thr225, which is also involved in the recognition of some but not all tumors. Asn216 and Thr125 both participate in the recognition of human beta cells, and the unknown ligand on *F. nucleatum*, does not require sialyation. This unique feature of NKp46, where it binds different ligands using diverse features and binding sites, has hindered research involving the function of NKp46. Furthermore, the biological relevance of the D1 domain of NKp46 remains elusive.

RELATED ART

PCT publication no. WO 2015/015489.

SUMMARY OF THE INVENTION

According to an aspect of some embodiments of the present invention there is provided an affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16.

According to an aspect of some embodiments of the present invention there is provided an affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16, conjugated to a toxic moiety.

According to an aspect of some embodiments of the present invention there is provided an isolated antibody comprising an amino acid sequence as set forth in SEQ ID NOs: 2 and 10.

According to an aspect of some embodiments of the present invention there is provided a pharmaceutical composition comprising as an active ingredient the affinity binding moiety of some embodiments of the invention, or antibody of some embodiments of the invention, and a pharmaceutically acceptable carrier.

According to an aspect of some embodiments of the present invention there is provided a method of preventing or treating a cancer associated with an expression of NKp46 in a subject in need thereof, the method comprising administering to the subject a therapeutically effective amount of the affinity binding moiety or antibody of some embodiments of the invention.

According to an aspect of some embodiments of the present invention there is provided a method of preventing or treating an autoimmune disease in a subject in need thereof, the method comprising administering to the subject a therapeutically effective amount of the affinity binding moiety of some embodiments of the invention, or antibody of some embodiments of the invention.

According to an aspect of some embodiments of the present invention there is provided an article of manufacture comprising the affinity binding moiety of some embodiments of the invention, or antibody of some embodiments of the invention, being packaged in a packaging material and identified in print, in or on the packaging material for use in the treatment of diabetes.

According to an aspect of some embodiments of the present invention there is provided an article of manufacture comprising the affinity binding moiety of some embodiments of the invention being packaged in a packaging material and identified in print, in or on the packaging material for use in the treatment of cancer associated with an expression of NKp46.

According to an aspect of some embodiments of the present invention there is provided an isolated polynucleotide encoding the affinity binding moiety of some embodiments of the invention.

According to an aspect of some embodiments of the present invention there is provided an isolated polynucleotide encoding the antibody of some embodiments of the invention.

According to an aspect of some embodiments of the present invention there is provided an expression vector comprising the isolated polynucleotide of some embodiments of the invention.

According to an aspect of some embodiments of the present invention there is provided a cell comprising the polynucleotide of some embodiments of the invention, or the expression vector of some embodiments of the invention.

According to an aspect of some embodiments of the present invention there is provided a method of detecting expression of NKp46 in a subject, the method comprising detecting expression of NKp46 in a biological sample of the subject by contacting the biological sample with the affinity binding moiety of some embodiments of the invention, or antibody of some embodiments of the invention, and detecting binding between the affinity binding moiety or antibody and the NKp46, thereby detecting expression of the NKp46 in the subject.

According to an aspect of some embodiments of the present invention there is provided a method of diagnosing an autoimmune disease or a cancer associated with an expression of NKp46 in a subject, the method comprising: (a) contacting a biological sample from the subject with the affinity binding moiety of some embodiments of the invention, or antibody of some embodiments of the invention, under conditions which allow the formation of immunocomplexes between NKp46 and the affinity binding moiety or the antibody; and (b) determining a level of the immunocomplexes in the biological sample, wherein an increase in level of the immunocomplexes beyond a predetermined threshold with respect to a level of the immunocomplexes in a biological sample from a healthy individual is indicative of the autoimmune disease or the cancer associated with the expression of NKp46.

According to an aspect of some embodiments of the present invention there is provided a method of diagnosing and treating an autoimmune disease or a cancer associated with an expression of NKp46 in a subject, the method comprising: (a) contacting a biological sample of the subject with the affinity binding moiety of some embodiments of the invention, or antibody of some embodiments of the invention, under conditions which allow the formation of immunocomplexes between NKp46 and the affinity binding moiety or the antibody; and (b) detecting expression of NKp46 immunocomplexes in the biological sample; (c) diagnosing the subject with autoimmune disease or a cancer associated with an expression of NKp46 when an increase in level of the immunocomplexes beyond a predetermined threshold with respect to a level of the immunocomplexes in a biological sample from a healthy individual; and (d) administering a therapeutic agent for the treatment of autoimmune disease or the cancer associated with an expression of NKp46 to the diagnosed subject, thereby diagnosing and treating autoimmune disease or the cancer associated with an expression of NKp46 in the subject.

According to an aspect of some embodiments of the present invention there is provided a method of monitoring treatment of a medicament for the treatment of an autoimmune disease or a cancer associated with an expression of NKp46, the method comprising: (a) treating a subject in need thereof with a medicament for the treatment of an autoimmune disease or a cancer associated with an expression of NKp46; and (b) detecting expression of NKp46 in a biological sample of the subject prior to and following the treatment, wherein the detecting the expression of the NKp46 is effected by contacting the biological sample with the affinity binding moiety of some embodiments of the invention, or antibody of some embodiments of the invention, and detecting binding between the affinity binding moiety or antibody and the NKp46, wherein a lower expression level of the NKp46 following the treatment as compared to the expression level of the NKp46 prior to the treatment is indicative of the efficient treatment.

According to some embodiments of the invention, the affinity binding moiety is an antibody or an antibody fragment.

According to some embodiments of the invention, the antibody fragment is selected from the group consisting of a Fab, F(ab')2, Fv, scFv, dsFv and a single domain molecule.

According to some embodiments of the invention, the antibody is conjugated to a therapeutic moiety.

According to some embodiments of the invention, the therapeutic moiety is selected from the group consisting of a cytotoxic moiety, a toxic moiety, a cytokine moiety and a drug.

According to some embodiments of the invention, the toxic moiety is a saporin toxin.

According to some embodiments of the invention, the cancer is a hematopoietic cancer.

According to some embodiments of the invention, the cancer is selected from the group consisting of an extranodal NK/T-cell lymphoma, a NK cell leukemia, a mycosis fungoides, an ALK+ anaplastic large cell lymphoma and a T-cell large granular lymphocyte (LGL) leukemia.

According to some embodiments of the invention, the method further comprises treating the subject with an additional anti-cancer agent or therapy.

According to some embodiments of the invention, the anti-cancer agent or therapy is selected from the group consisting of a chemotherapeutic agent, an antibody immunotherapy, a radiation therapy, a surgery, a cancer vaccine, an anti-inflammatory agent and a dietary supplement.

According to some embodiments of the invention, the autoimmune disease is diabetes.

According to some embodiments of the invention, the diabetes is type 1 diabetes.

According to some embodiments of the invention, the diabetes is type 2 diabetes.

According to some embodiments of the invention, the therapeutically effective amount results in an increase in blood insulin levels of the subject following the administering.

According to some embodiments of the invention, the therapeutically effective amount results in reduction in pancreatic beta cell destruction in the subject following the administering.

According to some embodiments of the invention, the therapeutically effective amount results in reduction in the amount of cancerous cells in the subject following the administering.

According to some embodiments of the invention, the article of manufacture further comprises insulin.

According to some embodiments of the invention, a nucleic acid sequence of the isolated polynucleotide is as set forth in heavy chain order N to C terminus SEQ ID NOs: 3, 5 and 7, and light chain order N to C terminus SEQ ID NOs: 11, 13 and 15.

According to some embodiments of the invention, a nucleic acid sequence of the isolated polynucleotide is as set forth in SEQ ID NOs: 1 and 9.

According to some embodiments of the invention, the method further comprises corroborating the diagnosis using a diagnostic assay selected from a blood test, an MRI or a CT scan.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 5A:
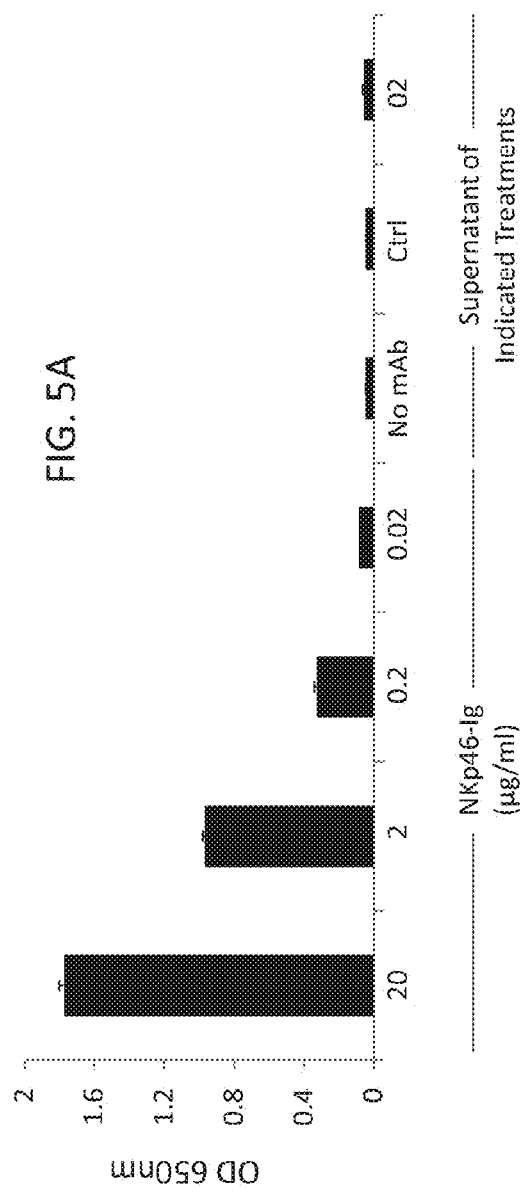

FIGS. 1A-B are graphs illustrating that several novel anti-NKp46 mAbs bind NKp46. FIG. 1A: FACS staining using anti-NKp46 mAbs (commercial anti-NKp46, 4G1G1, hNKp46.02, hNKp46.09, hNKp46.12) and a control mAb (12E7) of BW parental versus BW transfected cells expressing NKp46 (black and red histograms, respectively). The filled gray histogram represents staining with secondary antibody only of the BW parental cells. The background of BW NKp46 transfectants was similar and is not shown in the figure. Figure shows one representative experiment out of 6 performed; FIG. 1B: FACS staining using anti-NKp46 mAbs (commercial anti-NKp46, 4G1G1, hNKp46.02, hNKp46.09, hNKp46.12) and a control mAb (12E7) of IL-2 activated primary bulk human NK cells (black histogram). The filled gray histogram represents staining of NK cells with secondary antibody only. Figure shows one representative experiment out of 6 performed.

FIGS. 2A-C are graphs illustrating the characterization of several novel anti-NKp46 mAbs. FIG. 2A: NKp46-Ig was pre-incubated either alone (black histogram), with a control mAb or with anti-NKp46 mAbs (commercial anti-NKp46, 4G1G1, hNKp46.02, hNKp46.09, and hNKp46.12—red histograms) on ice, followed by FACS staining of BJAB cells with the pre-treated NKp46-Ig. The filled gray histogram represents staining of Bjab with secondary antibody only; FIG. 2B: Activated bulk NK cell cultures were incubated with the indicated anti-NKp46 mAbs (commercial anti-NKp46, 4G1G1, hNKp46.02, hNKp46.09, hNKp46.12) at 4° C. (black histogram) or at 37° C. (red histogram) for 8 hours, followed by FACS staining with a secondary antibody. The filled gray histogram represents staining with secondary antibody only of cells treated at 4° C. The background of cells treated at 37° C. was similar and is not shown in the figure. Figure shows one representative experiment out of 5 performed; FIG. 2C: Activated bulk NK cell cultures were incubated with ctrl (black histogram) and hNKp46.02 (red histogram) mAbs at 37° C. for 16 hours, followed by FACS staining of NK cells with the indicated different conjugated antibodies. The filled gray histogram represents staining of NK cells with isotype control antibody.

FIGS. 3A-C are graphs illustrating the time and concentration-dependent hNKp46.02-mediated NKp46 downregulation. FIGS. 3A-B: Incubation of activated bulk NK cells with 4G1G1 or hNKp46.02 mAbs for 8 hours at the indicated concentrations was performed either at 4° C. (FIG. 3A) or 37° C. (FIG. 3B), followed by FACS staining with anti-NKp46-APC. Background MFI values of isotype IgG-FITC control stainings were averaged and subtracted from all samples. Adjusted MFI values of the stainings were normalized to the lowest concentration checked (0.1 µg/ml) and set as 100%; FIG. 3C: Incubation of activated bulk NK cells with 5 µg/ml of either 4G1G1 or hNKp46.02 mAbs at 37° C. was performed for the indicated time points (1, 3, 5, 8, 16, and 24 hours) followed by FACS staining with anti-NKp46-FITC. Background MFI values of isotype IgG-FITC control stainings were averaged and subtracted from all samples. Adjusted MFI values were subsequently averaged and normalized to 4G1G1 (set as 100%). Shown are the mean values and SD derived from triplicates. *p<0.0005.

FIGS. 4A-E are graphs illustrating the effect of NKp46 downregulation by the hNKp46.02 mAb on NK cell function. FIGS. 4A-B: BW NKp46 transfectants were incubated either alone or with the indicated cancer cell lines (FIG. 4A) or with Jeg3 and Jeg3 incubated with influenza (Jeg3 PR8) (FIG. 4B) for 48 hours at 37° C., followed by ELISA for IL-2 secreted from BW NKp46 transfectants. IL-2 secretion was measured at OD 650 nm, and results were normalized to basal IL-2 secretion from BW NKp46 transfectants (set as 1). FIGS. 4A and 4B show one representative experiment out of at least 3 performed. Shown are the mean values and SD derived from triplicates. *p<0.05; FIGS. 4C-E: Activated bulk NK cells were initially incubated with 5 µg/ml of either ctrl or hNKp46.02 mAbs for 16 hours at 37° C. Cancer cell lines (FIG. 4C), Jeg3 in the presence of influenza (FIG. 4D), and human pancreatic beta cells (FIG. 4E) were then co-incubated with the NK cells and anti-CD107a APC and anti-CD56 PE antibodies for 2 hours at 37° C. Quadruplicate samples were plated and analyzed by FACS. Background MFI values of NK cells alone were averaged and subtracted from all samples. Adjusted MFI values were subsequently averaged and normalized to ctrl mAb (set at 100%). For FIGS. 4C, 4D and 4E, all experiments were performed at least twice with one representative replicate presented. Shown are the mean values and SD derived from quadruplicates. *p<0.05.

Figure 5B:
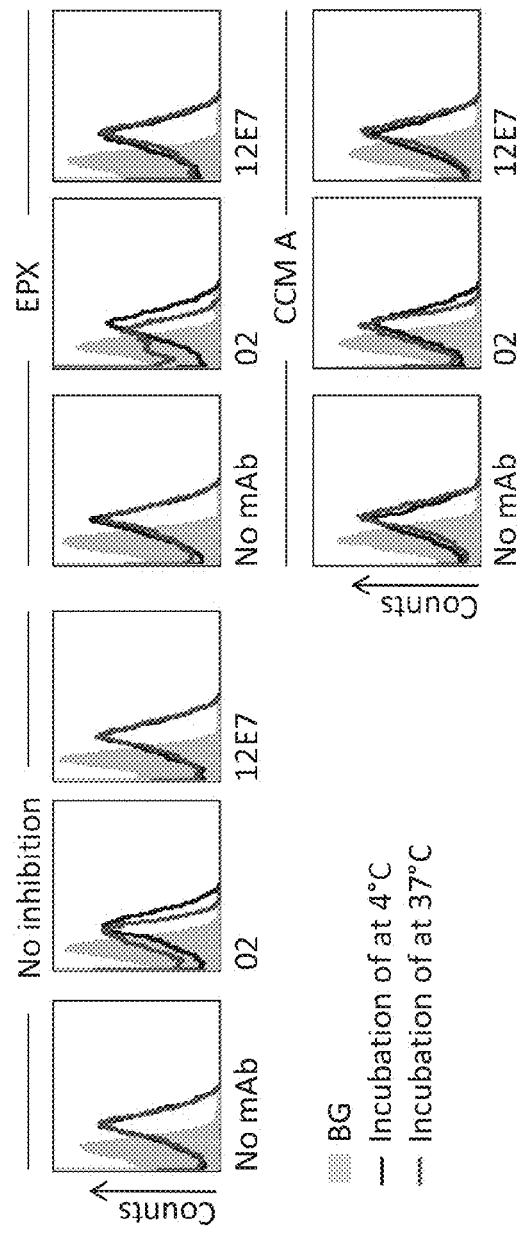

FIGS. 5A-B are graphs illustrating determination of the outcome of NKp46 on primary NK cells following binding of anti-NKp46 mAbs. FIG. 5A: Activated bulk NK cells were initially incubated either alone (No mAb) or with 5 µg/ml of ctrl or hNKp46.02 mAbs for 16 hours at 37° C. To determine if NKp46 is shed by the anti-NKp46 mAbs, supernatants of each treatment were collected and plated onto an ELISA plate. As a positive control for the direct ELISA, additional wells on the ELISA plate were coated with NKp46-Ig at the indicated concentrations. A biotinylated anti-NKp46 mAb was then used for detection of NKp46, and ELISA assays were performed. The figure shows one representative experiment out of 2 performed. Shown are the mean values and SD derived from triplicates; FIG. 5B: Activated bulk NK cells were initially incubated either alone or with proteosomal (EPX 0.5 ng/ml) or lysosomal (CCM A 20 nM) inhibitors for 20 minutes before the addition of 5 µg/ml of the mAbs (12E7, control and hNKp46.02, anti-NKp46) at 4° C. (black histogram) or 37° C. (red histogram) for 8 hours. This was followed by FACS staining of the cells with anti-NKp46 APC. The filled gray histogram represents staining with isotype control antibody only of cells treated at 4° C. The background of cells treated at 37° C. was similar and is not shown in the figure.

FIGS. 6A-C are graphs identifying and characterizing the binding sites of the anti-NKp46 antibodies. FIG. 6A: The fusion proteins, D1-Ig, D2-Ig, and NKp46-Ig were coated on ELISA plates overnight at 4° C. The anti-NKp46 antibodies (commercial anti-NKp46, 4G1G1, hNKp46.02, hNKp46.09, hNKp46.12) were subsequently added, followed by detection with a biotin anti-mouse antibody at OD 650 nm. Figure shows one representative experiment out of 2 performed. Shown are the mean values and SD derived from quadruplicates; FIG. 6B: 4G1G1 and hNKp46.02 binding to NKp46. A1-a5 was sequential addition of the hNKp46.02 mAb. "b" Test for saturation of the hNKp46.02 mAb on NKp46-derivatized chip. "c" Addition of 100 nM 4G1G1 onto hNKp46.02-saturated active surface produced a jump in response (ca 27RU). "d" addition of 100 nM hNKp46.02 solution did not affect the new baseline; FIG. 6C: The fusion proteins NKp46-Ig, D1-Ig and W32R-Ig were coated on ELISA plates overnight at 4° C. The anti-NKp46 antibodies (4G1G1, hNKp46.02) were subsequently added, followed by detection with a biotin anti-mouse antibody at OD 650 nm. Shown are the mean values and SD derived from quadruplicates.

FIGS. 7A-C are graphs illustrating that hNKp46.02 conjugated to a toxin inhibits cell proliferation. FIG. 7A: Activated bulk NK cells were plated at 2500 cells/well in RPMI overnight at 37° C. The next day, biotinylated 461-G1 and hNKp46.02 were conjugated to streptavidin-ZAP (461-G1-ZAP and hNKp46.02-ZAP, respectively) in an equal molar concentration of 10 nM. The conjugates were added to the NK cells and placed at 37° C. for 72 hours, after which an XTT cell viability assay was performed. Shown are the mean values and SD derived from sextuplicates. One representative assay is shown out of two performed. *p<0.05; FIG. 7B: YTS cells were incubated for 16 hours at 37° C. either alone (black histogram) or with 5 µg/ml of either 461-G1 or hNKp46.02 (green and red histograms respectively) followed by FACS staining with anti-NKp46 APC. The filled gray histogram represents staining of non-treated YTS cells with isotype control antibody (BG). The background of treated cells was similar and is not shown in the figure. One representative assay is shown out of two performed; FIG. 7C: YTS cells were plated at 2500 cells/well in RPMI overnight at 37° C. The next day, biotinylated 461-G1 and hNKp46.02 were conjugated to streptavidin-ZAP in an equal molar concentration of 0.01 pM. The conjugates were added to the YTS cells and placed at 37° C. for 72 hours, after which an XTT cell viability assay was performed. Shown are the mean values and SD derived from sextuplicates. *p<0.005.

DESCRIPTION OF SPECIFIC EMBODIMENTS OF THE INVENTION

The present invention, in some embodiments thereof, relates to novel NKp46 antibodies and, more particularly, but not exclusively, to the use of same for preventing and/or treating malignant and autoimmune diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Natural Killer (NK) cells are innate lymphocytes that efficiently eliminate cancer and infected cells. Their function is governed by a balance of signals transmitted by numerous inhibitory and activating receptors. NKp46 is one of the most important activating receptors found on all NK cells. Its role in the identification and elimination of various NK cell targets, ranging from viruses, bacteria, human beta cells, adipose cells, and tumor cells has been well established. The recognition of these various targets is mediated by one of its two extracellular domains, the membrane distal domain D1 and the membrane proximal domain D2. NKp46 utilizes different features and binding sites within its D2 domain to identify a large and dynamic repertoire of ligands. In contrast, the biological significance of the membrane distal domain, D1, of NKp46 has yet to be determined. Since NKp46 applies different features and binding sites to recognize its ligands, a single blocking monoclonal antibody may not be successful in inhibiting binding of NKp46 to all of its ligands.

While reducing the present invention to practice, the present inventors have developed a novel anti-human NKp46 monoclonal antibody, denoted hNKp46.02. The hNKp46.02 mAb is able to induce NKp46 internalization and degradation (see FIGS. 5A-B), hence eliminating the possibility of all ligand binding to NKp46 and subsequent activation. This antibody-mediated receptor internalization was achieved by hNKp46.02 binding to the D1 domain of NKp46 (see FIG. 6A). Interestingly, another anti-NKp46 mAb, 4G1G1, also bound the D1 domain, however this interaction did not affect the integrity (e.g. internalization) of NKp46. Accordingly, it was confirmed that 4G1G1 and hNKp46.02 have distinct binding sites on the D1 (see FIG. 6B). Thus, it is proposed that the D1 domain regulates receptor localization and stabilization. Moreover, downregulation of NKp46 by the hNKp46.02 mAb on the surface of NK cells significantly affected its activity against NKp46-dependent targets illustrating decreased killing of tumor cells, virally infected cells and beta cells (see FIGS. 4C-E, respectively).

The present inventors have further developed an antibody drug conjugate (ADC) in which the hNKp46.02 antibody was conjugated to a saporin toxin (termed herein hNKp46.02-ZAP). The toxin-conjugated hNKp46.02 antibody significantly inhibited NK cell growth (FIG. 7A) and tumor cell growth (FIG. 7C), thereby substantiating that the toxin conjugated hNKp46.02 antibody can be used in the treatment of autoimmune diseases and NKp46 expressing tumors.

Taken together, these results illustrate the potential of hNKp46.02 mAb as a therapeutic drug for the treatment of NKp46-dependent autoimmune diseases, such as, type 1 diabetes, and NKp46-expressing malignancies (such as NK cell lymphomas and T cell lymphomas).

Thus, according to one aspect of the present invention there is provided an affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16.

As used herein an "affinity binding moiety" refers to any naturally occurring or artificially produced molecule or composition which binds to a specific antigen with a higher affinity than to a non-specific antigen.

It should be noted that the affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66) using e.g. a captured or immobilized monoclonal antibody (MAb) format to minimize contribution of avidity, and can be calculated using, e.g., a dissociation constant, Kd, such that a lower Kd reflects a higher affinity.

As used herein the term "$K_D$" refers to the equilibrium dissociation constant between the antigen binding domain and its respective antigen.

According to a specific embodiment, the affinity binding moiety is an antibody or an antibody fragment.

The term "antibody" as used in this invention includes intact molecules as well as functional fragments thereof (that are capable of binding to an epitope of an antigen.

According to a specific embodiment, the antibody fragments include, but are not limited to, single chain, $F_{ab}$, $F_{ab'}$ and $F_{(ab')2}$ fragments, Fv, dsFv, scFvs, diabodies, minibodies, nanobodies, $F_{ab}$ expression library or single domain molecules such as VH and VL that are capable of binding to an epitope of the antigen in an HLA restricted manner.

The term "isolated" refers to at least partially separated from the natural environment e.g., from a cell.

As used herein, the "variable regions" and "CDRs" may refer to variable regions and CDRs defined by any approach known in the art, including combinations of approaches. According to a specific embodiment, the CDRs are determined according to Kabat.

According to an embodiment, SEQ ID NO: 4, SEQ ID NO: 6 and SEQ ID NO: 8 are arranged in a sequential order (N>C, as CDRs 1-3, respectively) on a heavy chain of the antibody, while SEQ ID NO: 12, SEQ ID NO: 14 and SEQ ID NO: 16 are arranged in a sequential order (N>C, as CDRs 1-3, respectively) on a light chain of the antibody.

According to one embodiment of the invention, the amino acid sequence comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, e.g., 100% sequence homology or identity to the peptide set forth in SEQ ID NOs: 4, 6, 8, 12, 14 or 16, wherein the peptide is capable of binding NKp46 (e.g. the D1 region of human NKp46).

Homology (e.g., percent homology, identity+similarity) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

For example, default parameters for tBLASTX include: Max target sequences: 100; Expected threshold: 10; Word size: 3; Max matches in a query range: 0; Scoring parameters: Matrix—BLOSUM62; filters and masking: Filter—low complexity regions.

According to a specific embodiment, the antibody is a humanized antibody.

According to a specific embodiment, the antibody is a chimeric antibody.

As used herein "a chimeric antibody" refers to an antibody in which at least one chain is of a non-human (e.g., murine) animal and a constant region [e.g., constant region e.g., CL (kappa or lambda)] is human. Thus, for example, the antibody can be a full antibody or a fragment thereof in which both chains comprise non-human variable regions and human constant regions. According to another example, one chain is humanized and another chain comprises non-human variable regions and human constant regions. A bi-specific configuration of a chimeric antibody is described hereinbelow.

Humanized forms of non-human (e.g., murine) antibodies are chimeric molecules of immunoglobulins, immunoglobulin chains which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse in this case, having the desired specificity, affinity and potency (cell killing). In some instances, Fv framework residues of the human immunoglobulin are replaced by corresponding non-human residues. Humanized antibodies may also comprise residues which are found neither in the recipient antibody nor in the imported CDR or framework sequences. The humanized antibody comprises all of the CDR regions corresponding to those of a non-human immunoglobulin and all or substantially all of the FR regions of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to one embodiment of the present invention, the antibody comprises an amino acid sequence as set forth in SEQ ID Nos: 2 and 10 (i.e. heavy chain and light chain, respectively).

According to one embodiment, the antibody is a bi-specific antibody.

According to one embodiment, the antibody comprises a therapeutic moiety.

According to one embodiment, the antibody comprises a detectable moiety.

These configurations will be discussed in detail herein-below.

As mentioned, the affinity binding moiety (e.g. antibody or antibody fragment) of the present invention is capable of binding NKp46.

The term "NKp46" as used herein refers to a human or non-human homolog, ortholog or isoform of the human natural cytotoxicity receptor known as NKp46, including for example those having GenBank Accession Nos. NP_001138929.1, NP_001138930.1, NP_001229285.1, NP_001229286.1 or NP_004820.1.

According to a specific embodiment the NKp46 is human.

According to one embodiment, the affinity binding moiety of the present invention binds the D1 region of human NKp46.

According to one embodiment, the affinity binding moiety of the present invention mediates NKp46 receptor internalization. Receptor internalization can be quantified using known methods, such as by FACS analysis (e.g. by treatment with the antibody of some embodiments of the invention followed by detection on the cell surface using flow cytometry), by treatment with lysosomal/proteosomal inhibitors (e.g. which would inhibit receptor degradation following internalization), and/or by confocal microscopy to confirm receptor internalization into lysosomes.

For expression, a nucleic acid sequence encoding the affinity binding moiety (e.g. antibody or antibody fragment) can be recombinantly expressed.

According to another embodiment of the present invention, the nucleic acid sequence comprises SEQ ID NOs: 1 and 9.

According to one embodiment of the present invention, the nucleic acid sequence comprises SEQ ID NOs: 3, 5, 7, 11, 13 and 15.

Also provided is an expression vector, comprising the isolated polynucleotide of some embodiments of the invention. According to one embodiment, the polynucleotide sequence is operably linked to a cis-acting regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion or presentation of antibody from a host cell in which it is placed. Preferably the signal sequence for this purpose is a mammalian signal sequence.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of TCRL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Improvements in recombinant polypeptide expression in mammalian cells can be achieved by effectively increasing the gene dosage in a transfected host cell. Increases in gene copy number are most commonly achieved by gene amplification using cell lines deficient in an enzyme such as dihydrofolate reductase (DHFR) or glutamine synthetase (GS) in conjunction with expression vectors containing genes encoding these enzymes and agents such as methotrexate (MTX), which inhibits DHFR, and methionine sulfoxamine (MSX), which inhibits GS. Thus, in an exemplary embodiment, expression vectors containing the recombinant gene under control of a strong promoter and genes encoding DHFR or GS, DHFR$^+$ or GS.sup$^+$ transfectants, respectively, can be obtained and gene amplification is then achieved by growing the transfectants in progressively increasing concentrations of MTX or MSX0.

Exemplary systems for expression are described in EP2861741, US20120178126, and US20080145895, each of which is incorporated herein by reference in its entirety.

Also provided are cells which comprise the polynucleotides/expression vectors as described herein.

Suitable host cells for cloning or expression of antibody-encoding vectors include prokaryotic or eukaryotic cells described herein. For example, antibodies may be produced in bacteria, in particular when glycosylation and Fc effector function are not needed. See also Charlton, Methods in Molecular Biology, Vol. 248 (B. K. C. Lo, ed., Humana Press, Totowa, N. J., 2003), pp. 245-254, describing expression of antibody fragments in E. coli. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR.sup.− CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Once antibodies are obtained, they may be tested for NKp46 binding affinities and induction of receptor internalization. Appropriate immunoassays for detecting specific antibody to NKp46 are known in the art and may be readily used for detecting antibodies according to the present invention. Suitable immunoassays include for example, radioimmunoassays, (RIA), fluorescent immunoassays, (FIA), enzyme-linked immunosorbant assays (ELISA), "sandwich" immunoassays, gel diffusion precipitation reactions, immunodiffusion assays, precipitation reactions, agglutination assays and immunoelectrophoresis assays [see for example, Harlow and Lane, Using Antibodies, A Laboratory Manual, Cold Spring Harbor Laboratory, New York (1999)]. Appropriate immunoassays for detecting induction of receptor internalization are described hereinabove.

The high specificity of the antibody renders it particularly suitable for therapeutic applications and for diagnostic.

According to one embodiment, the antibody may be attached to a heterologous therapeutic moiety (methods of conjugation are described hereinbelow). The therapeutic moiety can be, for example, a cytotoxic moiety, a toxic moiety, a cytokine moiety, a drug or an immunotoxin. Examples include, but are not limited to, toxins e.g., *Pseudomonas* exotoxin (e.g. *Pseudomonas* exotoxin PE38), Diphtheria toxin [e.g. Resimmune or A-dmDT390-bisFv (UCHT1)], Ricin A toxin, Saporin toxin, Gelonin toxin, Interleukin 2, Interleukin 4, Interleukin 10, CD3, CD16, or combinations thereof (e.g. Denileukin diftitox, an engineered protein combining Interleukin-2 and Diphtheria toxin). Immunotoxins are further described in Antignani and FitzGerald, *Toxins* (*Basel*) (2013) 5(8): 1486-1502, incorporated herein by reference.

According to a specific embodiment, the antibody is attached to a toxic moiety.

According to a specific embodiment, the antibody is attached to a Saporin toxin.

According to one embodiment, the antibody is an antibody-drug conjugate (ADC), i.e. a molecule comprising an antibody or antibody fragment linked to a biologically active cytotoxic agent (e.g. anti-cancer drug).

According to a specific embodiment, there is provided an affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16, conjugated to a toxic moiety.

According to a specific embodiment, there is provided an affinity binding moiety comprising an antigen recognition region which comprises complementarity determining region (CDR) amino acid sequences as set forth in heavy chain ordered N to C terminus: SEQ ID NOs: 4, 6 and 8, and light chain ordered N to C terminus: SEQ ID NOs: 12, 14 and 16, conjugated to a Saporin toxin.

According to one embodiment, the antibody is a bispecific antibody.

Bi-specific antibodies can be e.g. monoclonal antibodies that have binding specificities for at least two different antigens. For example, one of the binding specificities can be for NKp46 (e.g. D1 domain) and the other one is for any other antigen, for example a tumor ligand such as, but not limited to, PDL1, PVR, CEA. Methods of generating bi-specific antibodies are disclosed for example, in Suresh et al (Methods in Enzymology 121:210 (1986)).

The antibody may be in a soluble or insoluble form.

Examples of detectable moieties that can be used in the present invention for diagnostic applications include, but are not limited to, radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

Further examples of detectable moieties, include those detectable by Positron Emission Tomography (PET) and Magnetic Resonance Imaging (MRI), all of which are well known to those of skill in the art.

Exemplary detectable moieties include, but are not limited to, Streptavidin, Fluorescein isothiocyanate, Beta galactosidase, orange fluorescent protein, Biotin lygase tag, Myc tag, Histidine tag, Peroxidase, Alkaline phosphatase and Green Fluorescent protein.

When the detectable moiety is a polypeptide, the immunolabel (i.e. the antibody conjugated to the detectable moiety) may be produced by recombinant means or may be chemically synthesized by, for example, the stepwise addition of one or more amino acid residues in defined order using solid phase peptide synthetic techniques. Examples of polypeptide detectable moieties that can be linked to the antibodies of the present invention using recombinant DNA technology (in which the polynucleotide encoding the TCRL is translationally fused to the detectable moiety) include fluorescent polypeptides, phosphorescent polypeptides, enzymes and epitope tags.

Alternatively, chemical attachment of a detectable moiety to the antibodies of the present invention can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Thus, the conjugates described herein can be prepared by known methods of linking antibodies with lipids, carbohydrates, protein, toxins, drugs or other atoms and molecules. In some embodiments, the conjugate is formed by site-specific conjugation using a suitable linkage or bond. Site-specific conjugation is more likely to preserve the binding activity of the antibody. The substance may be conjugate or attached at the hinge region of a reduced antigen binding construct via thioether bond formation. In some embodiments, tyrosine conjugation can be employed. Other linkages or bonds used to form the conjugate can include, but are not limited to, a covalent bond, a non-covalent bond, a disulfide linkage, a hydrazone linkage, an ester linkage, an amido linkage, and amino linkage, an imino linkage, a thiosemicarbazone linkage, a semicarbazone linkage, an oxime linkage and a carbon-carbon linkage. In some embodiments, no cysteine or other linking aspect, need be included in antibody (Bioconjugate Techniques (Third Edition) Author(s): Greg T. Hermanson ISBN: 978-0-12-382239-0).

Exemplary methods for conjugating moieties are described in WO2017/027325 or U.S. Pat. No. 9,078,931 each of which is hereby incorporated by reference in its entirety.

Without being bound by theory, the present inventors have shown that binding of NKp46 using the novel antibody of the present invention induces receptor internalization and may thus be beneficial for delivery of therapeutic agents into NKp46 expressing pathogenic cells (e.g. cancer cells).

According to one embodiment, there is provided a method of preventing or treating a cancer associated with an expression of NKp46 in a subject in need thereof, the method comprising administering to the subject a therapeutically effective amount of the affinity binding moiety (e.g. antibody or antibody fragment) of some embodiments of the invention.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "preventing" refers to keeping a disease, disorder or condition from occurring in a subject who may be at risk for the disease, but has not yet been diagnosed as having the disease.

As used herein, the term "subject" refers to an animal, preferably a mammal, most preferably a human being, at any age or gender which may suffer from the pathology.

The term "cancer" as used herein is defined as disease characterized by the rapid and uncontrolled growth of aberrant cells. Cancer cells can spread locally or through the bloodstream and lymphatic system to other parts of the body.

According to the present invention, the cancer is associated with an expression of NKp46. Accordingly, the present invention can be used to treat any type of cancer in which at least some of the cells are NKp46 expressing cells.

According to one embodiment, the cancer is a hematopoietic cancer.

According to one embodiment, the cancer is a leukemia or a lymphoma.

According to one embodiment, the cancer is an NK cell cancer, a T cell cancer, a cutaneous T cell lymphoma (CTCL) or a cancer of large granular lymphocytes (LGLs).

According to a specific embodiment, the cancer is selected from the group consisting of an extranodal NK/T-cell lymphoma, a NK cell leukemia, a T cell large granular lymphocytic (LGL) leukemia, mycosis fungoides and an ALK+ anaplastic large cell lymphoma.

Diagnosis of a cancer associated with an expression of NKp46 is known to one of skill in the art. Thus, for example, blood tests (e.g. utilizing FACS analysis to determine the level of NKp46 expressing cells), ultrasound, CT scan, MRI, etc. may be used as known to one of skill in the art.

As mentioned above, NK cells may be involved in the etiology of autoimmune diseases. Specifically, NK cells may be involved in direct killing of tissue cells, which could lead to acceleration of autoimmunity. NK cells typically kill their targets by using NK killer receptors, including the NKp46 receptor. Without being bound by theory, binding of NKp46 using the novel antibody of the present invention may induce receptor internalization and degradation, and may thus be beneficial for the prevention or treatment of various autoimmune diseases.

According to one embodiment, there is provided a method of preventing or treating an autoimmune disease in a subject in need thereof, the method comprising administering to the subject a therapeutically effective amount of the affinity binding moiety (e.g. antibody or antibody fragment) of some embodiments of the invention.

As used herein, the term "autoimmune disease" refers to a disease where the body's immune system attacks its own cells or tissues. Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), inflammatory bowel disease (IBD) including Crohn's disease, ileitis and ulcerative colitis.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (MS, Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, the antibody of the present invention is administered to a subject with an autoimmune disease at disease onset, during disease remission, during an acute stage of the disease or during a chronic stage of the disease.

One specific use for the affinity binding moiety (e.g. antibody or antibody fragment) of the present invention is for preventing or treating diabetes in a subject in need thereof.

As used herein "Diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and may display, among other symptoms and signs, elevated blood glucose concentration, presence of glucose in the urine, excessive discharge of urine (polyuria), increased thirst (polydipsia) and increased hunger (polyphagia).

Symptoms may develop quite rapidly (e.g. within weeks or months) in type 1 diabetes, particularly in children. However, in type 2 diabetes symptoms may develop much more slowly and may be subtle or completely absent. Diabetes (both types) may also cause a rapid yet significant weight loss (despite normal or even increased eating) and irreducible mental fatigue. Diabetes as used herein encompasses any stage or type of diabetes, including, but not limited to, type 1 diabetes mellitus, type 2 diabetes mellitus, metabolic syndrome, insulin deficiency syndrome, overt diabetes, pre-diabetes, Latent autoimmune diabetes of adults (LADA), maturity onset diabetes of the young (MODY 1-11) and permanent neonatal diabetes mellitus.

According to one embodiment, the diabetes is type 1 diabetes.

According to one embodiment, the diabetes is type 2 diabetes.

According to one embodiment, the antibody of the present invention is administered to the subject at a stage of type 1 diabetes comprising pre-insulitis, early insulitis, pre-diabetes and/or overt diabetes.

According to another embodiment, the antibody of the present invention is administered to the subject at a stage of type 2 diabetes comprising hyperinsulinemia, pre-diabetes and/or overt diabetes.

Diagnosis of diabetes or of an autoimmune disease is known to one of skill in the art. Thus, for example, tests may be used to diagnose diabetes and pre-diabetes by measuring glucose and insulin levels (e.g. blood or urine levels), including for example, fasting plasma glucose (FPG) test, oral glucose tolerance test (OGTT), random plasma glucose (RPG) test, A1C test and serum insulin level test. Likewise, any number of tests may be used to diagnose autoimmune diseases (depending on the disease type and subject to be tested). Thus, for example, blood tests, ultrasound, CT scan, MRI, etc. may be used as known to one of skill in the art.

The affinity binding moiety (e.g. antibody or antibody fragment) of some embodiments of the invention can be administered to an organism per se, or in a pharmaceutical composition where it is mixed with suitable carriers or excipients.

Of note, the nucleic acid constructs described herein may also be used for in-vivo use where they are administered to a subject in need thereof (e.g., a subject with an autoimmune disease), as further described hereinbelow.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the affinity binding moiety (e.g. antibody or antibody fragment) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredient (i.e. affinity binding moiety, e.g. antibody or antibody fragment) effective to prevent, alleviate or ameliorate symptoms of a disorder (e.g., cancer or autoimmune disease such as diabetes) or prolong the survival of the subject being treated.

According to one embodiment, the therapeutically effective amount results in an increase in blood insulin levels and/or in reduction of blood glucose levels (e.g. to normal levels) of the subject following administration of the affinity binding moiety (e.g. antibody or antibody fragment).

Measurement of blood insulin levels and/or blood glucose levels is known to one of skill in the art, and is described in detail hereinabove.

According to one embodiment, the therapeutically effective amount results in reduction in pancreatic beta cell destruction in the subject following administration of the affinity binding moiety (e.g. antibody or antibody fragment).

Measurement of pancreatic cell mass may be used according to any method known in the art, as for example, by a biopsy, using magnetic resonance imaging (MRI) or using nuclear imaging techniques. Thus, for example measuring pancreatic cell mass may be carried out by using non-invasive imaging using agents that permit visualization of changes in $\beta$-cell mass e.g. using near-infrared fluorescent $\beta$-cell imaging agent or using a radioisotope-labeled fluorescent $\beta$-cell imaging agent as taught in Reiner et al., Proc Natl Acad Sci USA (2011) 108(31):12815-20; or using a $\beta$-cell-specific monoclonal antibody IC2, modified with a radioisotope chelator for nuclear imaging as taught in Moore et al. Diabetes (2001), Vol. 50(10): 2231-2236.

According to one embodiment, the therapeutically effective amount results in reduction in the amount of cancerous cells in the subject following administration of the affinity binding moiety (e.g. antibody or antibody fragment).

Measurement of levels of cancerous cells may be carried out using any method known in the art, as for example, by a biopsy, using magnetic resonance imaging (MRI) using nuclear imaging techniques, by CT scan, by ultrasound, or by blood tests (e.g. utilizing FACS analysis to determine the level of NKp46 expressing cells).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For any preparation used in the methods of the invention, the therapeutically effective amount or dose can be estimated from animal models (e.g. STZ diabetic mice, mouse xenograft model for NK cancer cells) to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition (e.g. cancer or autoimmune disease such as diabetes).

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the article of manufacture may further comprise another therapeutic composition for diabetes, e.g. insulin. Thus, for example, the antibodies or fragments thereof can be packaged in one container while insulin may be packaged in a second container both for therapeutic treatment.

According to an embodiment, the insulin composition may comprise any type of insulin known for therapeutics. Thus, for example, insulin of the invention may include rapid-acting insulin (e.g. which typically starts working within a few minutes and lasts for a couple of hours), regular- or short-acting insulin (e.g. which typically takes about 30 minutes to work fully and lasts for 3 to 6 hours, intermediate-acting insulin (e.g. which typically takes 2 to 4 hours to work fully and its effect can last for up to 18 hours), or long-acting insulin (e.g. for which there are typically no peak levels in the bloodstream, and can keep working for an entire day).

It will be appreciated that the article of manufacture may further comprise another therapeutic composition for cancer, e.g. anti-cancer drug. Thus, for example, the affinity binding moiety (e.g. antibody or antibody fragment) can be packaged in one container while anti-cancer drug may be packaged in a second container both for therapeutic treatment.

In certain embodiments of the present invention, and in order to improve disease treatment, the affinity binding moiety (e.g. antibody or antibody fragment) of some embodiments of the invention are effected in conjunction with any number of relevant therapeutic agents for the treatment of autoimmune diseases or anti-cancer therapies, including but not limited to, chemotherapy, radiation therapy, hormonal therapy, targeted therapy, immunotherapy, surgical therapy, cancer vaccine, anti-inflammatory agents and/or a dietary supplement. Such therapies and methods of utilizing same are well known to one of skill in the art.

As mentioned above, the affinity binding moiety (e.g. antibody or antibody fragment) of some embodiments of the invention is suitable for diagnostic applications.

According to an aspect of the present invention, there is provided a method of detecting expression of NKp46 in a subject, the method comprising detecting expression of NKp46 in a biological sample of the subject by contacting the biological sample with the affinity binding moiety (e.g. antibody or antibody fragment) of some embodiments of the invention and detecting binding between the affinity binding moiety (e.g. antibody or antibody fragment) and the NKp46, thereby detecting expression of the NKp46 in the subject.

The term "detecting", as used herein, refers to the act of detecting, perceiving, uncovering, exposing, visualizing or identifying a cell. The precise method of detecting is dependent on the detectable moiety (also referred to herein as identifiable moiety) to which the affinity binding moiety (e.g. antibody or antibody fragment) is attached as further described herein below.

As used herein "biological sample" refers to a sample of tissue or fluid isolated from a subject, including but not limited to, for example, plasma, serum, spinal fluid, lymph fluid, the external sections of the skin, respiratory, intestinal, and genitourinary tracts, tears, saliva, sputum, milk, blood cells, tumors, neuronal tissue, organs, and also samples of in vivo cell culture constituents. It should be noted that a "biological sample obtained from the subject" may also optionally comprise a sample that has not been physically removed from the subject, as described in greater detail below.

According to one embodiment, the biological sample contains cells or cell content.

The cells used by the present invention can be any cells which are derived from the subject. Examples include, but are not limited to, blood cells, bone marrow cells, hepatic cells, spleen cells, kidney cells, cardiac cells, skin cells (e.g., epithelial cells, fibroblasts, keratinocytes), lymph node cells, and fetal cells such as amniotic cells, placental cells (e.g., fetal trophoblasts) and/or cord blood cells.

Numerous well known tissue or fluid collection methods can be utilized to collect the biological sample or the cells from the subject in order to determine the level of DNA, RNA and/or polypeptide of the variant of interest in the subject (e.g. NKp46 expression).

Examples include, but are not limited to, fine needle biopsy, needle biopsy, core needle biopsy and surgical biopsy (e.g., brain biopsy), buccal smear and lavage. Regardless of the procedure employed, once a biopsy/sample is obtained the level of the variant can be determined and a diagnosis can thus be made.

The above-mentioned detection method can be harnessed to the diagnosis of an autoimmune disease or cancer associated with an expression of NKp46.

According to an aspect of the present invention, there is provided a method of diagnosing an autoimmune disease or a cancer associated with an expression of NKp46 in a subject, the method comprising: (a) contacting a biological sample from the subject with the affinity binding moiety (e.g. antibody or antibody fragment) of some embodiments of the invention, under conditions which allow the formation of immunocomplexes between NKp46 and the affinity binding moiety (e.g. antibody or antibody fragment); and (b) determining a level of the immunocomplexes in the biological sample, wherein an increase in level of the immunocomplexes beyond a predetermined threshold with respect to a level of the immunocomplexes in a biological sample from a healthy individual is indicative of the autoimmune disease or the cancer associated with the expression of NKp46.

According to an aspect of the present invention, there is provided a method of diagnosing and treating an autoimmune disease or a cancer associated with an expression of NKp46 in a subject, the method comprising: (a) contacting a biological sample of the subject with the affinity binding moiety (e.g. antibody or antibody fragment) of some embodiments of the invention, under conditions which allow the formation of immunocomplexes between NKp46 and the affinity binding moiety or the antibody; and (b) detecting expression of NKp46 immunocomplexes in the biological sample; (c) diagnosing the subject with autoimmune disease or a cancer associated with an expression of NKp46 when an increase in level of the immunocomplexes beyond a predetermined threshold with respect to a level of the immunocomplexes in a biological sample from a healthy individual; and (d) administering a therapeutic agent for the treatment of autoimmune disease or the cancer associated with an expression of NKp46 to the diagnosed subject, thereby diagnosing and treating autoimmune disease or the cancer associated with an expression of NKp46 in the subject.

According to one embodiment, a biological sample is obtained from the subject prior to contacting with an affinity binding moiety.

According to an aspect of the present invention, there is provided a method of monitoring treatment of a medicament for the treatment of an autoimmune disease or a cancer associated with an expression of NKp46, the method comprising: (a) treating a subject in need thereof with a medicament for the treatment of an autoimmune disease or a cancer associated with an expression of NKp46; and (b) detecting expression of NKp46 in a biological sample of the subject prior to and following the treatment, wherein detecting the expression of the NKp46 is effected by contacting the biological sample with the affinity binding moiety (e.g. antibody or antibody fragment) of some embodiments of the invention, and detecting binding between the affinity binding moiety or antibody and the NKp46, wherein a lower expression level of the NKp46 following the treatment as compared to the expression level of the NKp46 prior to the treatment is indicative of the efficient treatment.

According to one embodiment, the method further comprises obtaining a biological sample from subject prior to treating.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being check-up. Alternatively, the subject may be at risk of the disease. Yet alternatively, the method may be used to monitor treatment efficacy.

The affinity binding moiety (e.g. antibody or antibody fragment) may comprise e.g., be attached to an identifiable moiety. Alternatively or additionally, the affinity binding moiety (e.g. antibody or antibody fragment) may be identified indirectly such as by using a secondary antibody.

As mentioned, the method of the present invention is effected under conditions sufficient to form an immunocomplex (e.g. a complex between the affinity binding moiety (e.g. antibody or antibody fragment) of the present invention and the NKp46 peptide typically when expressed on a cell); such conditions (e.g., appropriate concentrations, buffers, temperatures, reaction times) as well as methods to optimize such conditions are known to those skilled in the art, and examples are disclosed herein below.

According to one embodiment, diagnosis is corroborated using any diagnostic method known in the art, e.g. blood test, MRI, ultrasound or CT scan.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to an antibody nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153;

3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Cells and Viruses

The cell lines used in this study were: 721.221, BCBL1, BJAB, C1R, Jeg3, and the murine thymoma BW cell line. NK cells were isolated from peripheral blood lymphocytes using the EasySep human NK enrichment kit (StemCells Technologies), and IL-2 activated bulk NK cells were cultured as previously described [Yamin et al., Cell Reports (2016) 15: 1542-1553]. Primary human beta cells were also used. The human influenza virus used in this study was the A/Puerto Rico/8/34 H1N1 (PR8) strain, and was generated as previously described [Achdout et al., J Immunol (2003) 171 (2) 915-923].

Antibodies and Fusion Proteins

The anti-NKp46 mAbs [4G1G1 (previously disclosed in Arnon et al. Blood (2004) 103:664-672), hNKp46.02, hNKp46.09, and hNKp46.12] were generated by the present inventors and required immunization of Ncr1$^{gfp/gfp}$ mice with NKp46-Ig fusion proteins. Control mAbs used in internalization experiments were anti-CD99 and anti-HLA.B7 (purified from hybridomas). FACS stainings were performed with the following antibodies (Abs): purified anti-NKp46, anti-NKp46 APC, anti-NKp46 FITC, anti-NKp44 APC, anti-NKp30 APC, anti-2B4 APC, anti-CD16 FITC, anti-DNAM1 FITC, anti-NKG2D PE, anti-CEACAM1 PE, anti-KIR2DL2 FITC, anti-KIR2DL1 FITC, anti-CD107a APC, and anti-CD56 PE, were purchased from Biolegend. Anti-TIGIT APC was purchased from eBioscience. Secondary isotype control Abs used in FACS stainings were: IgG FITC (IgG1), IgG PE (IgG2), and IgG APC (IgG1) which were purchased from Biolegend. Additional secondary Abs used in FACS stainings were: AlexaFluor 647-conjugated AffiniPure goat anti-mouse IgG and PE-conjugated AffiniPure donkey anti-human IgG, both purchased from Jackson ImmunoResearch. Purified anti-mouse IL-2 and biotinylated anti-mouse IL-2 mAbs purchased from Biolegend. The fusion proteins NKp46-Ig, D1-Ig, and D2-Ig were generated in HEK293T cells and purified, as previously described [Mandelboim et al., PNAS (1999) vol. 96(10): 5640-5644; Mandelboim et al. Nature (2001) 409: 1055-1060; Arnon (2004) supra].

Blocking Experiments

NKp46-Ig fusion proteins (3 µg/sample) were incubated either alone, with control (ctrl) or with anti-NKp46 mAbs (1 µg/sample) diluted in PBS×1, for 1 hour at 4° C. FACS staining with treated fusion proteins was then performed on BJAB cells.

NKp46 Receptor Downregulation Assays

Activated NK cells (50,000 cells/100 µl) were incubated for different time periods with either ctrl or anti-NKp46 mAbs at 4° C. or 37° C. (see figure legends for incubation times and concentrations used). After the allotted time period, cells were washed and stained with either a conjugated anti-NKp46 mAb or a conjugated secondary Ab, as indicated in the figure legends, followed by FACS analysis.

BW Reporter Assay

Murine thymoma BW cells were used to generate BW NKp46 transfectants which were subsequently used in BW assays, as previously described (Mandelboim et al. Nature (2001) supra). Briefly, BW NKp46 cells were incubated with irradiated (6000 rad) target cells at differing E:T ratios at 37° C. After 48 hours, supernatants were collected and IL-2 secretion levels were quantified by sandwich ELISA using anti-IL-2 mAbs.

CD107a Degranulation Assays

Analysis of CD107a on the surface on NK cells has been previously described [Alter et al. Journal of Immunological Methods (2004) 294:15-22]. The present inventors initially performed internalization assays on activated bulk NK cells incubated with 5 µg/ml of either ctrl or hNKp46.02 mAbs for 16 hours at 37° C. Target cells at different E:T ratios, anti-CD107a and anti-CD56 mABs were then added to the samples for 2 hours at 37° C. % CD107a on the NK cells was determined by FACS analysis.

Proteasome and Lysosome Inhibition

Activated bulk NK cells were incubated either alone or with the proteasome inhibitor, EPX, or the lysosomal inhibitor, CCM A, (both from Merck Milipore) for 20 minutes at 37° C. The ctrl and hNKp46.02 mAb were then added for an additional 8 hours at 37° C., followed by FACS staining with anti-NKp46 APC.

ELISA

NKp46 Surface Shedding:

Supernatants (150 µl) from a 16 hours internalization assay with activated bulk NK cells incubated with ctrl or hNKp46.02 mAbs were collected and placed on ELISA plates overnight at 4° C. As a positive control, NKp46-Ig was plated at the indicated concentrations. Blocking was performed with (PBS×1/Tween 0.05%/BSA 1%), followed by addition of a biotinylated anti-NKp46 mAb at 1 µg/ml diluted in blocking buffer. Streptavidin-HRP was then added and detection with TMB was measured at OD 650 nm.

Determining Binding Site of Anti-NKp46 mAbs:

The fusion proteins (NKp46-Ig, D1-Ig, D2-Ig, and W32R-Ig) were first plated at 1 µg/ml diluted in PBS×1. Blocking was performed with (PBS×1/Tween 0.05%/BSA 1%), followed by addition of the anti-NKp46 mAbs at 1 µg/ml diluted in blocking buffer. Biotin anti-mouse was subsequently added followed by streptavidin-HRP, and detection with TMB was measured at OD 650 nm.

Determining Distinct Binding Sites Using Surface Plasmon Resonance (SPR)

Surface Plasmon Resonance using Biacore T100 was used to discriminate between hNKp46.02 and 4G1G1 for binding on NKp46. The NKp46-Ig fusion protein was dissolved in 10 mM Sodium acetate buffer, pH 5 at 10 µg/ml. This solution was used to immobilize NKp46-Ig to CM5 Series S chip using a standard amine coupling protocol to the level of about 500RU. hNKp46.02 Saturation of NKp46 active surface was accomplished by 5 consecutive 1 minute injections of 1 µM hNKp46.02 solution in the running buffer (10 mM HEPES 150 mM NaCl 3 mM EDTA, 0.05% Tween20, pH 7.3) at flow rate of 20 µL/min. After that, 4G1G1 was injected at 100 nM for 1 minute at flow rate of 20 µL/min.

Finally, an injection of 100 nM of hNKp46.02 was performed to confirm that active surface is still saturated with respect to hNKp46.02.

hNKp46.02 Conjugation to Toxin Followed by XTT Viability Assay

The antibodies, 461-G1 and hNKp46.02, were initially biotinylated using EZ-link Sulfo-NHS-SS-Biotin according to the manufacturer's instructions (ThermoFisher Scientific 21331). Once biotinylated, the antibodies were conjugated to the toxin saporin, which itself was attached to streptavidin (Streptavidin-ZAP), as purchased from ATSbio. Conjugation of the antibodies to the toxin (denoted as antibody-ZAP), treatment of the cells, and the XTT cell viability assay were performed according to the manufacturer's instructions (Biotin-Z Internalization Kit KIT-27-Z100, ATSbio).

Example 1

Generation of Anti-NKp46 mAb: hNKp46.02

To develop antibodies against NKp46, NKp46-deficient mice (Ncr1$^{gfp/gfp}$) were injected with a fusion protein consisting of the extracellular portion of NKp46 fused to human IgG. New anti-NKp46 mAbs were evaluated for their ability to bind NKp46. Binding was initially examined on mouse thymoma BW transfectant cells expressing NKp46 (BW NKp46). As controls, a commercially available anti-NKp46 mAb and an anti-NKp46 mAb previously developed in the inventor's lab, 4G1G1, were used. Three new anti-NKp46 mAbs were generated and shown in FIG. 1A, namely hNKp46.02, hNKp46.09 and hNKp46.12, that similarly to the commercial anti-NKp46 mAb and to 4G1G1, specifically interact with BW NKp46 but not with the parental BW cells. To demonstrate that the new anti-NKp46 mAbs recognize NKp46 naturally expressed by human NK cells, IL-2 activated primary bulk human NK cells (activated NK cells) were stained and observed for recognition by all anti-NKp46 mAbs (FIG. 1B).

Example 2

Binding of NKp46 by the hNKp46.02 mAb LED to NKp46 Downregulation from the Surface of NK Cells The present inventors initially wanted to check whether any of the new anti-NKp46 mAbs could block the interaction of NKp46 with its ligands. Since the present inventors were especially interested in developing anti-NKp46 mAbs that can inhibit binding of NKp46 to its unknown tumor ligand/s, the BJAB tumor cells were used that express an unknown ligand for NKp46 (FIG. 2A). NKp46-Ig was incubated either alone or with the various anti-NKp46 mAbs on ice, followed by FACS staining of BJAB cells with the treated NKp46-Ig fusion proteins. None of the anti-NKp46 mAbs were able to block the binding of NKp46-Ig to the cells (FIG. 2A), suggesting that the anti-NKp46 mAbs are not blocking mAbs. The present inventors next tested whether one of the anti-NKp46 mAbs could leads to NKp46 downregulation from the surface of NK cells. The anti-NKp46 mAbs were incubated with activated NK cells for 8 hours either at 4° C. or 37° C. The cells were then FACS stained with a conjugated secondary anti-mouse antibody. Interestingly, it was observed that only one mAb, hNKp46.02, lead to the downregulation of NKp46 from the surface of the cells (FIG. 2B). To confirm that the downregulation was specific, the assay was repeated on activated NK cells with the hNKp46.02 mAb and a control mAb, followed by FACS staining against a large repertoire of NK cell receptors, both activating and inhibitory. The results demonstrated that the hNKp46.02 mAb-mediated downregulation was specific against NKp46 (FIG. 2C). Similar results were obtained using activated NK cells from various donors.

The next step was to optimize the NKp46 downregulation mediated by the hNKp46.02 mAb. Accordingly, a dose-dependent assay was carried out in which activated NK cells were incubated with various concentrations of 4G1G1 (used as control) and hNKp46.02 mAbs for 8 hours at either 4° C. or 37° C. (FIGS. 3A and 3B, respectively). At 4° C. there was no downregulation of NKp46. The minimum amount of the hNKp46.02 mAb that induced the maximum NKp46 downregulation (an approximate 40% decrease in surface expression at 8 hours FIG. 3B) was 0.5 µg per 50,000 NK cells (FIG. 3B). Greater amounts of the hNKp46.02 mAb did not yield further downregulation of the receptor from the surface. Taking these results into consideration, a time-course assay was performed with activated NK cells incubated with the 4G1G1 and hNKp46.02 mAbs at 0.5 µg per 50,000 NK cells. After 16 hours, the hNKp46.02 mAb lead to a decrease in NKp46 surface expression by approximately 60%, which was maintained even after 24 hours (FIG. 3C).

Example 3

NKp46 Receptor Downregulation Mediated by hNKp46.02 Impedes NK Cell Activation Against Target Cells To determine whether NKp46 downregulation by the hNKp46.02 mAb would have an effect on the functionality of NK cells, the present inventors first needed to find target cells that would lead to NKp46-dependent NK cell activation. As such, a cell based reporter system was used which involves mouse thymoma BW cells (BW cells). These cells were transfected with a chimeric protein composed of the extracellular portion of NKp46 fused to the mouse ζ-chain (BW NKp46, shown in FIG. 1A). Engagement of the receptor with its ligand leads to secretion of IL-2, which is then quantified by ELISA assay. Various cancer cell lines were assayed in this system, and a select few, 721.221, BCBL1, BJAB and C1R, were chosen for presentation based on their consistent and significant activation of BW NKp46 (FIG. 4A). Jeg3 cells, which are known to not express NKp46 ligands, were incubated with influenza and used as a positive control for the assay. Influenza-Jeg3 cells express the hemagglutinin (HA) protein of influenza, which is a well-established viral ligand of NKp46. As can be seen in FIG. 4B, Jeg3 cells incubated with BW NKp46 induced no significant IL-2 secretion, as opposed to influenza-Jeg3 cells which lead to a significant increase in IL-2 secretion.

The above described target cells were then used to examine the functionality of the hNKp46.02 mAb. CD107a degranulation assays were performed on activated NK cells immediately after they were incubated with either a control or the hNKp46.02 mAbs for 16 hours. As can be seen in FIG. 4C, activated NK cells which were incubated with the hNKp46.02 mAb prior to the degranulation assays displayed a significant decrease in their % CD107a when incubated with 721.221, BCBL1, BJAB and C1R cells, indicating that their activation potential was inhibited by the hNKp46.02 mAb. Similarly, activated NK cells previously incubated with the hNKp46.02 mAb, had lower % CD107a when incubated with Jeg3 cells in the presence of influenza (FIG.

4D). Interestingly, Jurkat and K562 cells did not induce a decrease in activation of NK cells incubated with hNKp46.02 (FIG. 4C), indicating that the NKp46 ligand they express is not critically important for their elimination by NK cells. Taken together, these results display the ability of hNKp46.02 to distinguish between target cells which express an NKp46 ligand to those whose elimination is NKp46-dependent.

Previous work has demonstrated in both human and mouse models of type I diabetes, that NK cells interact with and destroy beta cells, in an NKp46-dependent manner [Gur et al., *J Immunol.* (2011) 187(6):3096-103]. Consequently, the present inventors tested whether NKp46 downregulation by the hNKp46.02 mAb on activated NK cells would prevent killing of human beta cells. FACS analysis revealed a drastic decrease in % CD107a of approximately 65%, indicating that the hNKp46.02 mAb strongly inhibited NK cells from killing human beta cells (FIG. 4E).

Example 4

Mechanism of hNKp46.02-Mediated NKp46 Downregulation

The hNKp46.02-mediated downregulation of NKp46 can either be due to receptor shedding or internalization followed by degradation. To test whether NKp46 is shed following hNKp46.02 mAb incubation with NK cells, the amount of NKp46 in the supernatants was monitored. Activated NK cells were incubated either alone or with control or hNKp46.02 mAbs for 16 hours at 37° C. Supernatants were collected and plated onto ELISA plates. As a positive control for the assay, NKp46-Ig was also plated on the ELISA plate. FIG. 5A shows that in the supernatant of NK cells incubated either alone or with the control or hNKp46.02 mAbs, NKp46-Ig was detected, but not NKp46. From these results it was therefore concluded that the hNKp46.02 mAb probably doesn't cause shedding of NKp46 from the surface of NK cells and instead might lead to NKp46 internalization.

To test whether NKp46 is internalized and degraded, activated NK cells were treated with either proteasome (EPX) or lysosomal (CCM A) inhibitors before performing incubation with the control or the hNKp46.02 mAbs. As can be seen in FIG. 5B, NKp46 expression was reduced by the hNKp46.02 mAb on activated NK cells that were not treated with an inhibitor and those treated with the proteasome inhibitor. Interestingly, NKp46 expression was not reduced when the NK cells were initially treated with a lysosomal inhibitor; thus indicating that NKp46 undergoes lysosomal degradation upon internalization by the hNKp46.02 mAb.

Example 5 hNKp46.02 Binds a Particular Site on the D1 Domain of NKp46

The present inventors wanted to characterize the binding site of the hNKp46.02 mAb on NKp46. NKp46 is composed of two domains, D1 and D2. Fusion proteins comprised of the D1 or D2 domains fused to human IgG were prepared (D1-Ig and D2-Ig, respectively) and used in a direct ELISA assays (FIG. 6A). Interestingly, the hNKp46.02 mAb bound the D1 domain. Moreover, it bound the same domain as the commercial and 4G1G1 anti-NKp46 mAbs which were previously illustrated as not inducing receptor downregulation (see FIG. 2B). Consequently, the present inventors wanted to determine whether the hNKp46.02 mAb had a unique binding site on the D1 domain, distinct to that of 4G1G1. Therefore, the use of surface plasmon resonance (SPR) was applied. The NKp46-Ig fusion protein was immobilized onto a chip, followed by injection of the anti-NKp46 mAbs. The hNKp46.02 mAb was injected first, and then 4G1G1 was injected. 4G1G1 was able to bind NKp46-Ig even after it was saturated with the hNKp46.02 mAb (indicated by the red arrow in FIG. 6B). These results demonstrated that the hNKp46.02 and 4G1G1 mAbs have different binding sites on the D1 domain.

As previously mentioned, NKp46 is the only NCR to have a mouse orthologue, denoted Ncr1. A mutation in Ncr1 at position 32, where tryptophan was replaced with arginine resulted in receptor accumulation in the ER. Since this mutation occurs at the D1 domain of the receptor the present inventors wondered whether this mutation on the human NKp46 will affect hNKp46.02 mAb binding. For this, the tryptophan residue in position 32 of human NKp46 was mutated and was replaced with arginine. Fusion proteins were generated consisting of the extracellular mutated NKp46 fused to human IgG (W32R-Ig), and used in a direct ELISA assay. As can be seen in FIG. 6C, both 4G1G1 and hNKp46.02 mAbs bind the mutated NKp46 protein, however, significantly less as comparted to the D1-Ig or the wild type NKp46-Ig. Hence, although the mutation in position 32 probably affects protein folding, the hNKp46.02 binding site is not confined to this exact position.

Example 6 hNKp46.02 as a Therapeutic mAb

NKp46 has been implicated as a critical player in the progression and severity of different diseases, including type I diabetes, or as a prognostic marker for NK cell malignancies, and approximately 20% of T cell lymphomas. Consequently, the present inventors investigated the potential use of hNKp46.02 antibody conjugated to drug (e.g., toxin) as an immunotherapeutic drug, such as for the treatment of these diseases. hNKp46.02 was conjugated to the saporin toxin (termed hNKp46.02-ZAP), hypothesizing that once the antibody undergoes cellular internalization it will introduce the toxin into the cell and thereby lead to cell death. The toxin used, saporin, is a ribosome inactivating protein which cannot enter cells on its own. As a control, the antibody 461-G1 was conjugated to the toxin (termed 461-G1-ZAP). 461-G1 was previously shown to bind NKp46 but does not induce internalization (FIGS. 2B and 3A-C).

The conjugates (461-G1-ZAP and hNKp46.02-ZAP) were incubated with either activated NK cells (FIG. 7A) or the NK tumor cell line, YTS (FIGS. 7B-C) for 72 hours, followed by a cell viability assay. The ability of hNKp46.02 to induce NKp46 internalization on YTS cells was also confirmed before proceeding with the assay (FIG. 7B). As can be seen in FIG. 7A, NK cells treated with hNKp46.02-ZAP were severely inhibited indicating the potential of this conjugate in treating NKp46-dependent autoimmune diseases, such as type I diabetes. Furthermore, as illustrated in FIG. 7C, the significant capability of hNKp46.02-ZAP in inhibiting tumor cell growth was demonstrated. Taken together, these results exemplify the great potential of hNKp46.02 as an antibody drug conjugate (ADC), which can be used to treat NKp46-dependent diseases and various NKp46-expressing malignancies, such as NK cell lymphomas and T cell lymphomas.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody or antibody fragment that binds to NKp46 comprising at least the antigen recognition region, wherein the antigen recognition region comprises the complementarity determining region (CDR) amino acid sequences contained in a monoclonal antibody comprising heavy chain variable region set forth in SEQ ID NO: 2 and light chain variable region sequence set forth in SEQ ID NO: 10.

2. The antibody or antibody fragment according to claim 1, comprising the CDR amino acid sequences set forth in heavy chain ordered N to C terminus: SEQ ID NOs: 4, 6 and 8, and light chain ordered N to C terminus: SEQ ID NOs: 12, 14 and 16.

3. The antibody of claim 1, comprising a heavy chain variable region set forth in SEQ ID NO: 2 and a light chain variable region sequence set forth in SEQ ID NO: 10.

4. The antibody fragment of claim 1 selected from the group consisting of a Fab, F(ab')2, Fv, scFv, dsFv and a single domain molecule.

5. The antibody or antibody fragment of claim 1, wherein said antibody or antibody fragment is conjugated to a therapeutic moiety.

6. The antibody or antibody fragment of claim 5, wherein said therapeutic moiety is selected from the group consisting of a cytotoxic moiety, a toxic moiety, a cytokine moiety, a drug and an immunotoxin.

7. The antibody or antibody fragment of claim 6, wherein said toxic moiety is selected from the group consisting of *Pseudomonas* exotoxin, Diphtheria toxin, Ricin A toxin, Saporin toxin and Gelonin toxin.

8. The antibody or antibody fragment of claim 5, wherein said therapeutic moiety is selected from the group consisting of Interleukin 2, Interleukin 4, Interleukin 10, CD3, CD16, and combinations thereof.

9. The antibody or antibody fragment of claim 6, wherein said toxic moiety is a saporin toxin.

10. A pharmaceutical composition comprising as an active ingredient the antibody or antibody fragment of claim 1, and a pharmaceutically acceptable carrier.

11. An antibody or antibody fragment drug conjugate comprising an antigen recognition region and a toxic moiety, wherein the antibody or antibody fragment drug conjugate comprising an antigen recognition region comprises heavy chain CDR amino acid sequences as set forth in SEQ ID NOs: 4, 6 and 8, and light chain CDR sequences set forth in SEQ ID NOs: 12, 14 and 16.

12. The antibody or antibody fragment drug conjugate of claim 11, wherein said toxic moiety is a saporin toxin.

13. A pharmaceutical composition comprising as an active ingredient the antibody or antibody fragment drug conjugate of claim 11, and a pharmaceutically acceptable carrier.

14. A method of eliminating a population of NK cells, comprising contacting a cell population of NK cells expressing NKp46 with the antibody or antibody fragment drug conjugate of claim 11, wherein binding of said antibody or antibody fragment drug conjugate induces NKp46 internalization and killing.

15. A method of treating a cancer associated with expression of NKp46 in a subject in need thereof, the method comprising administering to the subject a therapeutically effective amount of the antibody or antibody fragment of claim 5.

16. The method of claim 15, wherein said cancer is a hematopoietic cancer.

17. The method of claim 15, wherein the cancer is selected from the group consisting of an extranodal NK/T-cell lymphoma, a NK cell leukemia, a mycosis fungoides, an ALK+ anaplastic large cell lymphoma and a T-cell large granular lymphocyte (LGL) leukemia.

18. The method of claim 15, further comprising treating said subject with an additional anti-cancer agent or therapy.

19. The method of claim 18, wherein said anti-cancer agent or therapy is selected from the group consisting of a chemotherapeutic agent, an antibody immunotherapy, a radiation therapy, a surgery, a cancer vaccine, an anti-inflammatory agent and a dietary supplement.

20. The method of claim 15, wherein said therapeutically effective amount results in reduction in the amount of cancerous cells in the subject following said administering.

21. An article of manufacture comprising the antibody or antibody fragment of claim 5 being packaged in a packaging material and identified in print, in or on said packaging material for use in the treatment of cancer associated with an expression of NKp46.

22. An isolated polynucleotide encoding the antibody or antibody fragment of claim 1.

23. The isolated polynucleotide of claim 22, wherein a nucleic acid sequence of said isolated polynucleotide is as set forth in heavy chain order N to C terminus SEQ ID NOs: 3, 5 and 7, and light chain order N to C terminus SEQ ID NOs: 11, 13 and 15.

24. The isolated polynucleotide of claim 22 encoding an antibody comprising a heavy chain variable region set forth in SEQ ID NO: 2 and a light chain variable region sequence set forth in SEQ ID NO: 10.

25. The isolated polynucleotide of claim 24, wherein a nucleic acid sequence of said isolated polynucleotide is as set forth in SEQ ID NOs: 1 and 9.

26. The isolated polynucleotide of claim 22 encoding an antibody fragment selected from the group consisting of a Fab, F(ab')2, Fv, scFv, dsFv and a single domain molecule.

27. An expression vector comprising the isolated polynucleotide of claim 22.

28. A cell comprising the polynucleotide of claim 22.

29. A method of detecting expression of NKp46 in a biological sample, the method comprising contacting said biological sample with the antibody or antibody fragment of claim 1, and detecting binding between said antibody or antibody fragment and the NKp46, thereby detecting expression of said NKp46 in the biological sample.

30. The method of claim 29, wherein the biological sample is from a subject diagnosed with cancer.

31. A method of diagnosing a disease associated with an expression of NKp46 in a subject, the method comprising: (a) contacting a biological sample from the subject with the antibody or antibody fragment of claim 1, under conditions which allow the formation of immunocomplexes between NKp46 and said antibody or antibody fragment; and (b) determining a level of said immunocomplexes in said biological sample, wherein an increase in the level of said immunocomplexes above a predetermined threshold is indicative of the disease associated with the expression of NKp46, wherein the predetermined threshold is the level of said immunocomplexes in a biological sample from a healthy individual.

32. The method of claim 31, wherein the disease associated with an expression of NKp46 is cancer.

33. A method of diagnosing and treating a cancer associated with an expression of NKp46 in a subject, the method comprising: (a) contacting a biological sample of the subject with the antibody of claim 1, under conditions which allow the formation of immunocomplexes between NKp46 and said antibody or antibody fragment; and (b) detecting the level of NKp46 immunocomplexes in said biological sample; (c) diagnosing the subject with a cancer that is associated with an expression of NKp46 when an increase in the level of said immunocomplexes is higher than a predetermined threshold, where the predetermined threshold is the level of said immunocomplexes in a biological sample from a healthy individual; and (d) administering a therapeutic agent for the treatment of said cancer associated with an expression of NKp46 to the diagnosed subject, thereby diagnosing and treating the cancer associated with an expression of NKp46 in the subject.

34. The method of claim 33, further comprising corroborating the diagnosis using a diagnostic assay selected from a blood test, an MRI or a CT scan.

35. A method of monitoring treatment of a subject having cancer associated with an expression of NKp46, the method comprising: (a) treating a subject in need thereof with a medicament for the treatment of a cancer associated with an expression of NKp46; and (b) detecting expression of NKp46 in a first biological sample of the subject prior to and second biological sample following said treatment, wherein said detecting comprises contacting the first and second biological samples with the antibody or antibody fragment of claim 1, and detecting binding between said antibody or antibody fragment and the NKp46, wherein a lower expression level of NKp46 in the second biological sample following said treatment as compared to said expression level of NKp46 in the first biological sample prior to said treatment is indicative that the treatment is effective.

36. The method of claim 15, wherein said subject is a human subject.

37. The antibody or antibody fragment of claim 1, wherein the antibody is a monoclonal antibody.

\* \* \* \* \*